(12) United States Patent
Talebpour et al.

(10) Patent No.: US 9,063,136 B2
(45) Date of Patent: Jun. 23, 2015

(54) CELL CONCENTRATION, CAPTURE AND LYSIS DEVICES AND METHODS OF USE THEREOF

(75) Inventors: Samad Talebpour, Richmond Hill (CA); Aye Aye Khine, Thornhill (CA); Stephen W. Leonard, Unionville (CA); Robert Maaskant, King City (CA); Tino Alavie, Thornhill (CA)

(73) Assignee: QVELLA CORPORATION, Richmond Hill, ON (CA)

( * ) Notice: Subject to any disclaimer, the term of this patent is extended or adjusted under 35 U.S.C. 154(b) by 428 days.

(21) Appl. No.: 13/388,654

(22) PCT Filed: Jul. 30, 2010

(86) PCT No.: PCT/CA2010/001176
§ 371 (c)(1),
(2), (4) Date: Apr. 16, 2012

(87) PCT Pub. No.: WO2011/014946
PCT Pub. Date: Feb. 10, 2011

(65) Prior Publication Data
US 2012/0190040 A1    Jul. 26, 2012

Related U.S. Application Data

(60) Provisional application No. 61/287,253, filed on Dec. 17, 2009, provisional application No. 61/230,738, filed on Aug. 2, 2009, provisional application No. 61/230,740, filed on Aug. 2, 2009.

(51) Int. Cl.
*G01N 33/543* (2006.01)
*B01L 3/00* (2006.01)
(Continued)

(52) U.S. Cl.
CPC ....... *G01N 33/5438* (2013.01); *B01L 3/502715* (2013.01); *B01L 3/502753* (2013.01);
(Continued)

(58) Field of Classification Search
None
See application file for complete search history.

(56) References Cited

U.S. PATENT DOCUMENTS 5,344,535 A * 9/1994 Betts et al. ............. 204/547
6,071,394 A * 6/2000 Cheng et al. ........... 204/547
(Continued)

FOREIGN PATENT DOCUMENTS

JP    2008/054511 A    3/2008
WO    99/38612 A1    8/1999

OTHER PUBLICATIONS

Brychzy, A. et al, "Cofactor Tpr2 combines two TPR domains and a J domain to regulate the Hsp70/Hap90 chaperone system" EMBO J. Jul. 15, 2003 (Mar. 15, 2003), vol. 22, No. 14, pp. 3613-3623, ISSN 0261 4189, see "Materials and Methods"csection and Figure 2.

*Primary Examiner* — Bao Thuy L Nguyen
*Assistant Examiner* — Gary E Hollinden
(74) *Attorney, Agent, or Firm* — Lynn C. Schumacher; Stephen W. Leonard; Hill & Schumacher

(57) ABSTRACT

The present invention provides a microfluidic devices and methods of use thereof for the concentration and capture of cells. A pulsed non-Faradaic electric field is applied relative to a sample under laminar flow, which results to the concentration and capture of charged analyte. Advantageously, pulse timing is selected to avoid problems associated with ionic screening within the channel. At least one of the electrodes within the channel is coated with an insulating layer to prevent a Faradaic current from flowing in the channel. Under pulsed application of a unipolar voltage to the electrodes, charged analyte within the sample is moved towards one of the electrodes via a transient electrophoretic force.

27 Claims, 15 Drawing Sheets

(51) Int. Cl.
*C12M 3/06* (2006.01)
*C12M 1/12* (2006.01)
*C12M 1/00* (2006.01)
*C12M 1/42* (2006.01)
*C12M 1/34* (2006.01)
*C12N 1/06* (2006.01)
*C12N 11/14* (2006.01)
*C12N 13/00* (2006.01)
*G01N 33/50* (2006.01)

(52) U.S. Cl.
CPC .............. *C12M23/16* (2013.01); *C12M 25/00* (2013.01); *C12M 25/04* (2013.01); *C12M 29/10* (2013.01); *C12M 35/02* (2013.01); *C12M 41/38* (2013.01); *C12N 1/066* (2013.01); *C12N 11/14* (2013.01); *C12N 13/00* (2013.01); *G01N 33/5005* (2013.01)

(56) References Cited

U.S. PATENT DOCUMENTS

| | | | |
|---|---|---|---|
| 6,440,725 B1* | 8/2002 | Pourahmadi et al. | 435/288.5 |
| 7,135,421 B2 | 11/2006 | Ahn et al. | |
| 2002/0042125 A1* | 4/2002 | Petersen et al. | 435/287.2 |
| 2002/0090649 A1* | 7/2002 | Chan et al. | 435/7.1 |
| 2003/0113713 A1* | 6/2003 | Glezer et al. | 435/5 |
| 2003/0124572 A1* | 7/2003 | Umek et al. | 435/6 |
| 2004/0011650 A1* | 1/2004 | Zenhausern et al. | 204/547 |
| 2008/0014589 A1* | 1/2008 | Link et al. | 435/6 |

* cited by examiner

CELL CONCENTRATION, CAPTURE AND LYSIS DEVICES AND METHODS OF USE THEREOF

CROSS-REFERENCE TO RELATED APPLICATION

This application is a National Phase application claiming the benefit of PCT/CA2010/001176 filed on Jul. 30, 2010, in English, which further claims priority to U.S. Provisional Application No. 61/230,740, titled "DIAGNOSTIC METHODS AND DEVICES INCORPORATING ELECTRO-LYSIS OF BOUND CELLULAR ARRAYS" and filed on Aug. 2, 2009, the entire contents of which are incorporated herein by reference; U.S. Provisional Application No. 61/230,738, titled "LATERAL FLOW DEVICES AND METHODS FOR THE DETECTION OF CELLULAR ANALYTE" and filed on Aug. 2, 2009, the entire contents of which are incorporated herein by reference, and U.S. Provisional Application No. 61/287,253, titled "CELL CONCENTRATION AND CAPTURE DEVICE AND METHOD OF USE THEREOF" and filed on Dec. 17, 2009, the entire contents of which are incorporated herein by reference.

FIELD OF THE INVENTION

This invention relates to in-vitro diagnostic methods and devices for the concentration and/or detection of cellular analytes. More particularly, the invention relates to microfluidic diagnostic devices involving the concentration and capture of cells and the controlled permeabilization or lysis of cells.

BACKGROUND OF THE INVENTION

Increasing the sensitivity and reducing assay run time is often important for detecting and identifying microorganisms in clinical and environmental samples. For example, in the case of sepsis diagnosis, even a moderate increase in sensitivity or a decrease in assay time can have life or death consequences for a patient. In cell affinity assays in which increased sensitivity is required, it is common to augment the concentration of cell numbers at the proximity of the capture ligands, and to attempt to increase the frequency at which the cells collide with the capture ligands. Sample concentration, in the case of cellular samples, is routinely performed by centrifugation or filtration followed by cell re-suspension in an appropriate liquid media. Unfortunately, the processes require several time consuming manual steps and are not easily amenable to automation in a cost effective manner.

While some solutions have proposed the use of electric fields for the concentration and capture of species, such methods typically still require complex sample preparation steps in order to obtain a precisely controlled ionic environment. For example, in prior art devices adapted to produce concentration using electrophoretic concentration, it is usually necessary to re-suspend the sample in a buffer with a low ionic strength and/or to include oxidation and reduction reagents to avoid or mitigate electrolytic effects. A failure to address these effects results in problems associated with the difficulty of establishing an electric field inside a raw or minimally treated aqueous sample due to screening effects of the dissolved ions, and the onset of electrochemical reactions, such as water electrolysis, at the electrode-electrolyte interfaces. Such limitations impair the utility of electrical sample concentration approaches due to the onerous and costly pre-processing steps.

What is therefore needed is an integrated device that allows for the rapid concentration of analyte and the subsequent detection of a sample, without requiring significant pre-treatment of the sample.

SUMMARY OF THE INVENTION

In a first aspect, there is provided an apparatus for detecting an intracellular analyte, the apparatus comprising: a solid support comprising an immobilization region, the immobilization region having provided thereon an adherent material for immobilizing one or more cells provided in a cell-containing liquid sample; the immobilization region further comprising secondary receptors for binding intracellular analyte released from the cells.

The adherent material preferably comprises primary receptors having an affinity for a surface of the cells, where the primary receptors are preferably antibodies. The secondary receptors may be immobilized to the adherent material. The adherent material may be capable of immobilizing more than one cell type or genus. The secondary receptors are preferably selected from the group consisting of antibodies, aptamers, nucleic acids, and nucleic acid analogs. The cells may be prokaryotic cells wherein the intracellular analyte comprises a nucleic acid. The intracellular analyte is preferably specific to a type of the cell or a cell genus.

The apparatus may comprise one or more additional immobilization regions, wherein the immobilization region and the additional immobilization regions form an array, and where each immobilization region preferably selective to a different intracellular analyte. The adherent material within each immobilization region preferably is selective to a unique cell type or genus. Each immobilization region is preferably provided for detecting a unique type, species, strain, and/or genus of a microorganism.

In one aspect, the solid support may be a surface of a microwell.

In another aspect, the solid support may be an internal surface of a microfluidic channel, and may further comprise electrodes for electrically releasing contents of immobilized cells, wherein the solid support comprises: a first electrode; a second electrode defining an internal surface of the microfluidic channel facing the solid support; and a dielectric layer provided on the first electrode for preventing the flow of a Faradaic current within the microfluidic channel under the application of a voltage between the first and second electrodes, wherein the adherent material and the secondary receptors are provided on the dielectric layer. The thickness of the dielectric layer and a dielectric constant of the dielectric layer are preferably selected to provide an amplified transient electric field proximal to the dielectric layer within the microfluidic channel under the application of a voltage pulse between the first and second electrodes.

The thickness of the dielectric layer is preferably in the range of approximately 10 nm to 100 nm, and the dielectric constant of the dielectric layer is preferably within a range of approximately 3 to 10. The dielectric layer is preferably aluminum oxide, and the first electrode is preferably aluminum. The second electrode is preferably a transparent electrode.

The microfluidic channel may further comprise: an electrical concentration zone upstream of the immobilization region for concentrating cells within the liquid sample when the liquid sample is contacted with the microfluidic channel, wherein the cells may be concentrated toward an upstream portion of the solid support prior to flowing the cells downstream to the immobilization region under the application of an electric field.

The concentration zone may comprise a portion of the microfluidic channel in which the first and second electrodes extend upstream of the immobilization zone, wherein the cells may be concentrated to the upstream portion of the solid support under the application of a series of unipolar voltage pulses between the first and second electrodes. Alternatively, the concentration zone may comprise additional electrodes provided on opposing sides of the microfluidic channel upstream of the first and second electrodes, wherein the cells may be concentrated to the upstream portion of the solid support under the application of a series of unipolar voltage pulses between the additional electrodes.

The secondary receptors may be provided adjacent to the adherent material within the immobilization region, or may be co-mixed with the adherent material within the immobilization region.

In another aspect, there is provided a system for detecting an intracellular analyte, the system comprising the apparatus as described above, the system further comprising a liquid handling means for contacting the sample with the solid support.

In yet another aspect, there is provided a system for detecting an intracellular analyte, the system comprising the apparatus described above, the system further comprising a pulsed voltage source for applying one or more voltage pulses between the first and second electrodes.

In still another aspect, there is provided a method of providing an immobilization region on a solid support for immobilizing one or more cells and binding intracellular analyte from the one or more cells, the method comprising: providing the solid support, wherein the solid support comprises a surface functionalized to bind an adherent material and secondary receptors, wherein the adherent material has an affinity for a surface of the one or more cells and the secondary receptors are selected to bind the intracellular analyte; dispensing one or more liquid reagents comprising the adherent material and the secondary receptors onto a localized region of the solid support; and drying the solid support.

The step of dispensing the one or more liquid reagents may comprise dispensing a pre-mixed reagent comprising the adherent material and the secondary receptors. The adherent material and the secondary receptors preferably comprise functional groups for covalently binding to the functionalized surface. The functionalized surface preferably comprises a heterobifunctional silane layer.

In another aspect, there is provided a microfluidic device for disrupting a cellular membrane of a cell, the device comprising: a microfluidic channel for flowing a cell containing liquid sample; a first electrode provided on one surface of the microfluidic channel; a second electrode provided on an opposing surface of the microfluidic channel; and a dielectric layer provided on the first electrode for preventing the flow of a Faradaic current within the microfluidic channel under the application of a voltage between the first and second electrodes; wherein a thickness of the dielectric layer and a dielectric constant of the dielectric layer are selected to provide an amplified transient electric field proximal to the dielectric layer within the microfluidic channel under the application of a voltage pulse between the first and second electrodes.

The dielectric layer preferably comprises an immobilization region, the immobilization region having provided thereon an adherent material for immobilizing one or more cells provided by the cell-containing liquid sample. A thickness of the dielectric layer is preferably in the range of approximately 10 nm to 100 nm, and a dielectric constant of the dielectric layer is preferably within a range of approximately 3 to 10. The dielectric layer is preferably aluminum oxide.

The microfluidic channel may further comprise: an electrical concentration zone upstream of the immobilization region for concentrating cells within the liquid sample when the liquid sample is contacted with the microfluidic channel, wherein the cells may be concentrated toward an upstream portion of a surface of the microfluidic channel, the surface provided on a common side of the microfluidic channel relative to the immobilization region, prior to flowing the cells downstream to the immobilization region under the application of an electric field. The concentration zone preferably comprises a portion of the microfluidic channel in which the first and second electrodes extend upstream of the immobilization zone, wherein the cells may be concentrated to the surface under the application of a series of unipolar voltage pulses between the first and second electrodes. The concentration zone may alternatively comprise third and fourth electrodes provided on opposing sides of the microfluidic channel upstream of the first and second electrodes, wherein the cells may be concentrated to the surface under the application of a series of unipolar voltage pulses between the third and fourth electrodes.

In another aspect, there is provided a system for disrupting a cellular membrane of a cell, the system comprising the apparatus according to the above apparatus, the system further comprising a liquid handling means for contacting the liquid sample with microfluidic channel. The system further may further comprise a pulsed voltage source for applying one or more voltage pulses between the first and second electrodes.

In yet another aspect, there is provided a method of disrupting a cellular membrane of one or more cells provided in a cell-containing liquid sample, the method comprising the steps of: providing a microfluidic device comprising: a microfluidic channel; a first electrode provided on one surface of the microfluidic channel; a second electrode provided on an opposing surface of the microfluidic channel; and a dielectric layer provided on the first electrode for preventing the flow of a Faradaic current within the microfluidic channel under the application of a voltage between the first and second electrodes, the dielectric layer comprising an immobilization region, the immobilization region having provided thereon an adherent material for immobilizing cells; flowing the liquid sample through the microfluidic channel, wherein one or more cells of the cell-containing liquid sample are immobilized by the immobilization region; applying one or more voltage pulses to the electrodes, the voltage pulses having a time duration and an amplitude selected to disrupting a cellular membrane of the immobilized cells; wherein a thickness of the dielectric layer and a dielectric constant of the dielectric layer are selected to provide an amplified transient electric field proximal to the dielectric layer within the microfluidic channel under the application of the voltage pulses between the first and second electrodes. The amplified transient electric field preferably exceeds an electric field that would be obtained in the absence of the dielectric layer.

The method may further comprise the step of flowing a wash reagent through the microfluidic channel prior to the step of applying one or more voltage pulses to the electrodes.

An ionic strength of the cell-containing liquid sample is preferably selected to be less than 100 mM. Each pulse of the voltage pulses preferably comprises a time duration on a millisecond to sub-millisecond timescale.

The disruption of the cellular membrane may comprises the electroporation or electro-lysis of the cellular membrane.

The immobilization region may further comprise secondary receptors for binding intracellular analyte released from the immobilized cells, the method further comprising the steps of: performing additional assay steps to detect intracellular analyte bound to the secondary receptors. The additional assay steps may comprise flowing a detector reagent into the microfluidic channel, the detector reagent comprising a labeled receptor specific to the intracellular analyte; and flowing a wash reagent through the microfluidic channel; and detecting a signal from detector reagent bound to the bound intracellular analyte.

The intracellular analyte preferably comprises a nucleic acid and the secondary receptors preferably comprise probes for binding to the nucleic acid. The nucleic acid may comprise rRNA and wherein the probes comprise one of a DNA probe and a synthetic DNA analog probe.

The method may further comprise the step of filling the microfluidic channel with a buffer comprising an ionic strength of less than approximately 10 mM prior to the step of applying one or more voltage pulses to the electrodes. The method may further comprise, where the immobilization region further comprises secondary receptors for binding the intracellular analyte, the steps of: performing additional assay steps to detect intracellular analyte bound to the secondary receptors.

The intracellular analyte is charged, in which case prior to the step of performing the additional assay steps to detect the intracellular analyte bound to the secondary receptors, the following step may be performed: applying a series of unipolar voltage pulses between the first and second electrodes after having released the intracellular analyte; wherein a polarity of the unipolar voltage pulses is selected to concentrate the intracellular analyte proximal to the secondary receptors. The liquid sample may comprises a raw biological sample, and the method may comprise screening the raw sample for the presence or absence of microorganisms.

Prior to the step of performing the additional assay steps to detect the intracellular analyte bound to the secondary receptors, the method may further comprise the step of filling the microfluidic channel with an additional reagent while applying the unipolar voltage pulses, the additional reagent selected to support binding between the intracellular analyte and the secondary receptors.

The additional assay steps may comprise: flowing a detector reagent into the microfluidic channel, the detector reagent comprising a labeled receptor specific to the intracellular analyte; and flowing a wash reagent through the microfluidic channel; and detecting a signal from detector reagent bound to the bound intracellular analyte.

The intracellular analyte may comprise a nucleic acid, wherein the secondary receptors comprise probes for binding to the nucleic acid, and the additional reagent comprises a hybridization buffer. The nucleic acid preferably comprises rRNA and the probes preferably comprise a DNA probe or a synthetic DNA analog probe.

The method may further comprise the following steps: prior to the step of applying one or more voltage pulses to the electrodes, flowing a detection reagent through the microfluidic channel, the detection reagent selected to produce a signal when the detection reagent contacts intracellular analyte released from the immobilized cells; and after applying the one or more voltage pulses, detecting the signal. The signal is preferably an optical signal, in which case the second electrode is transparent. The intracellular analyte is preferably adenosine triphosphate, and wherein the detection reagent comprises luciferin and luciferase.

The device may further comprises one or more additional immobilization regions, wherein the immobilization region and the additional immobilization regions form an array. Each the immobilization region is preferably selective to a different intracellular analyte. The adherent material within each the immobilization region is preferably selective to a unique cell type or genus. Each immobilization region is preferably provided for detecting a unique type, species, strain, and/or genus of a microorganism.

In yet another aspect, there is provided a method of concentrating electrically charged cells within a cell-containing liquid sample, the method comprising the steps of: providing a microfluidic device comprising: a microfluidic channel; a first electrode provided on one surface of the microfluidic channel; a second electrode provided on an opposing surface of the microfluidic channel; and a dielectric layer provided on one of the first and second electrodes for preventing the flow of a Faradaic current within the microfluidic channel under the application of a voltage between the first and second electrodes; flowing the liquid sample through the microfluidic channel; applying a series of unipolar voltage pulses between the first and second electrodes, wherein the unipolar voltage pulses have a polarity selected to apply an electrophoretic force directed toward a selected side of the microfluidic channel. The liquid sample may comprise a concentration of ions, and wherein the ratio of a mobility to a diffusivity of the charged species significantly exceeds the ratio of a mobility to a diffusivity of the ions.

The method preferably further comprises the step of flowing a wash liquid through the fluidic device while applying the unipolar voltage pulses.

A time duration of each voltage pulse is preferably less than approximately a timescale over which an electrical field within the fluidic channel is screened by ions within the sample. An interval between voltage pulses is preferably greater than approximately a diffusive relaxation time of ions within the sample. A duration of each voltage pulse is preferably greater than about 1 microsecond and less than about 10 milliseconds. An interval between voltage pulses is preferably greater than about ten times the pulse duration, and/or is approximately within the range of 10 microseconds to 100 millisecond.

The method may further comprising performing the following steps prior to applying the series of voltage pulses: applying one or more voltage pulses between the first pair of electrodes, wherein the voltage has a polarity selected to apply an electrophoretic force to the charged species in a direction towards the side of the fluidic channel common to one of the first pair of electrodes, measuring a current applied to the pair of electrodes while applying the one or more voltage pulses; and selecting a preferred pulse duration for use when applying the series of voltage pulses by determining a time interval between the time at which a voltage pulse is applied and the time at which the measured current drops below a selected minimum current threshold.

The minimum current threshold may be selected to be a fraction of the current measured immediately after a given voltage pulse is applied. Alternatively, the current may be fitted to a exponential function, and wherein the minimum current threshold is selected to be approximately equal to the current measured at a time approximately equal to a fitted time constant.

The sample may be flowed through the fluidic device using an external pump means, and the sample may be recirculated through the fluidic device one or more times. A motion of the sample may be oscillated within the fluidic device one or more times.

The pump means may be an external pump, wherein the external pump is coupled to the device through tubing and a fluidic interfacing means connected to an inlet port of the device, or a pipettor, wherein the pipettor comprises a pipette tip adapted to be inserted into an inlet port of the device. An absorbent material may be provided downstream of a channel outlet of the device is adapted to induce flow of liquid in the channel.

The method may further comprise filtering the sample, wherein the fluidic device comprises at least one filter apparatus. The filter apparatus may comprise packed ion exchange resins.

In a case where the cells are microorganisms and wherein the selected surface of the microfluidic channel further comprises an adherent material for immobilizing the microorganisms on the selected side of the microfluidic channel, the method preferably further comprising the steps of: monitoring an optical signal indicative of an accumulation of the microorganisms on the selected side of the microfluidic channel through a transparent surface of the microfluidic channel while flowing the sample; after a pre-selected accumulation level has been obtained, flowing a wash reagent through the microfluidic channel; providing a growth medium into the microfluidic channel; incubating the channel for a first time interval while monitoring growth of microorganisms bound by the adherent material by measuring the optical signal; flowing a wash reagent through the microfluidic channel; providing a growth medium inoculated with an antibiotic into the microfluidic channel; measuring the optical signal to determine a baseline signal; incubating the microfluidic channel for a second time interval while monitoring growth of the microorganisms bound by the adherent material in the presence of the antibiotic by measuring the optical signal; and determining growth rate by from a difference between the signal obtained in the presence of the antibiotic and the baseline signal.

The optical signal may comprise an auto-fluorescence signal from the cells. The method may alternatively comprise contacting the cell-containing liquid sample with a labeled detector reagent prior to the step of flowing the sample through the microfluidic channel, the labeled detector reagent comprising receptors having an affinity for a surface of the cells, the label comprising a fluorometric label, and wherein the optical signal comprises a fluorescence signal from the labeled detector reagent bound to the cells. The method may alternatively comprise contacting the cell-containing liquid sample with a fluorometric stain prior to the step of flowing the sample through the microfluidic channel, wherein the optical signal comprises a fluorescence signal from the fluorometric stain bound to the cells.

The method preferably further comprises the step of inferring a susceptibility of the microorganism to the antibiotic from the growth rate.

In another aspect, wherein the selected side is a side of the microfluidic channel where the dielectric layer is located, the method further may further comprise the steps of: applying one or more voltage pulses to the electrodes, the voltage pulses having a time duration and an amplitude selected to disrupting a cellular membrane of the cells concentrated proximal to the dielectric layer; wherein a thickness of the dielectric layer and a dielectric constant of the dielectric layer are selected to provide an amplified transient electric field proximal to the dielectric layer within the microfluidic channel under the application of the voltage pulses between the first and second electrodes.

In yet another aspect, there is provided a device for detecting intracellular analyte, the device comprising: a lateral flow apparatus comprising, in fluid-flow contact with one another, a sample receiving zone for receiving a fluid sample and a capture zone comprising an immobilized capture reagent that binds directly or indirectly to one or more cellular analytes; and an upper electrode in fluid-flow contact with a top surface of the capture zone and a lower electrode in fluid-flow contact with a bottom surface of the capture zone when the capture zone is moistened by a fluid sample. The device further comprises a voltage source for applying a voltage between the upper and lower electrodes, and may further comprise one or more reagents for detecting the intracellular analyte.

The intracellular analyte preferably comprises adenosine-5'-triphosphate and wherein the one or more reagents comprise luciferin and luciferase.

The one or more reagents are preferably dried within one of the capture zone and the sample receiving zone, or are immobilized in one of the capture zone and an additional zone downstream of the capture zone.

The one or more reagents preferably comprise receptors for binding the intracellular reagent, and are more preferably antibodies, aptamers, or nucleic acid probes (or synthetic analogs thereof).

The device may further comprise a labeled detection reagent for producing a measurable signal from intracellular analyte bound to the one or more reagents.

The upper electrode is preferably a transparent electrode, and a spacing between the upper and lower electrodes is preferably less than approximately 100 microns. A voltage of the voltage source and a spacing of between the upper and lower electrodes is preferably selected to be capable of providing an internal electric field between the upper and lower electrodes that is greater than about 1 kV/cm.

The device preferably further comprises a means for applying a compressive force to the upper electrode.

A further understanding of the functional and advantageous aspects of the invention can be realized by reference to the following detailed description and drawings.

BRIEF DESCRIPTION OF THE DRAWINGS

The embodiments of the present invention are described with reference to the attached figures, wherein.

DETAILED DESCRIPTION OF THE INVENTION

Figure 1:
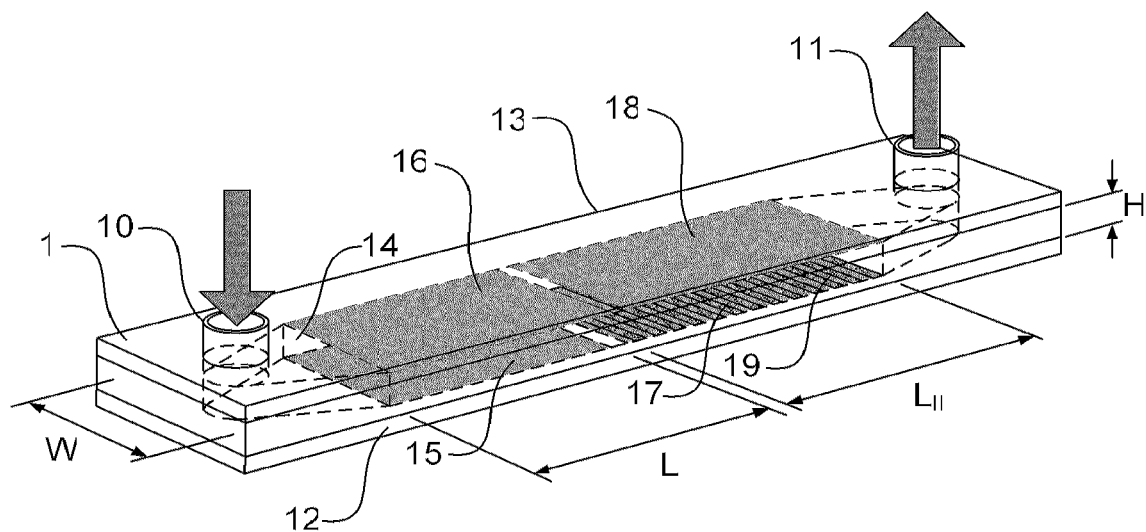
FIG. 1 shows a schematic of a microfluidic device having concentration and reaction zones.

Generally speaking, the systems described herein are directed to devices for the concentration, capture and detection of cellular analyte. As required, embodiments of the present invention are disclosed herein. However, the disclosed embodiments are merely exemplary, and it should be understood that the invention may be embodied in many various and alternative forms. The Figures are not to scale and some features may be exaggerated or minimized to show details of particular elements while related elements may have been eliminated to prevent obscuring novel aspects. Therefore, specific structural and functional details disclosed herein are not to be interpreted as limiting but merely as a basis for the claims and as a representative basis for teaching one skilled in the art to variously employ the present invention. For purposes of teaching and not limitation, the illustrated embodiments are directed to devices and methods adapted to concentrate and detect cellular or membrane bound analyte.

As used herein, the terms, "comprises" and "comprising" are to be construed as being inclusive and open ended, and not exclusive. Specifically, when used in this specification including claims, the terms, "comprises" and "comprising" and variations thereof mean the specified features, steps or components are included. These terms are not to be interpreted to exclude the presence of other features, steps or components.

As used herein, the terms "about" and "approximately", when used in conjunction with ranges of dimensions of particles, compositions of mixtures or other physical properties or characteristics, are meant to cover slight variations that may exist in the upper and lower limits of the ranges of dimensions so as to not exclude embodiments where on average most of the dimensions are satisfied but where statistically dimensions may exist outside this region. It is not the intention to exclude embodiments such as these from the present invention.

As used herein, the coordinating conjunction "and/or" is meant to be a selection between a logical disjunction and a logical conjunction of the adjacent words, phrases, or clauses. Specifically, the phrase "X and/or Y" is meant to be interpreted as one or both of X and Y" wherein X and Y are any word, phrase, or clause.

"Array" and "array surface" as used herein are to be interpreted broadly and generally relate to a linear or two-dimensional array of discrete immobilization regions (here at least two), each having a finite area, formed on a solid support, usually on a continuous surface thereof, and supporting one or more binding agents. Ordered arrays of nucleic acids, proteins, small molecules, cells or other substances on a solid support enable parallel analysis of complex biochemical samples.

"Immobilization region" as used herein relates to a localized area on the solid support surface for binding one or more cells or intracellular analyte released from one or more cell. The immobilization region may have any desired shape, such as circular, rectangular, elliptical, etc, and is often referred to as a "spot".

"Solid support" as used herein is meant to comprise any solid (flexible or rigid) substrate onto which it is desired to apply an array of one or more binding agents. The substrate may be biological, non-biological, organic, inorganic or a combination thereof, and may be in the form of particles, strands, precipitates, gels, sheets, tubing, spheres, containers, capillaries, pads, slices, films, plates, slides, etc, having any convenient shape, including disc, sphere, circle, etc. The substrate surface supporting the array may have any two-dimensional configuration and may include, for example steps, ridges, kinks, terraces and the like and may be the surface of a layer of material different from that of the rest of the substrate.

"Specific binding pair" (abbreviated "sbp") as used herein describes a pair of molecules (each being a member of a specific binding pair) which are naturally derived or synthetically produced. One of the pair of molecules has a structure (such as an area or cavity) on its surface that specifically binds to (and is therefore defined as complementary with) a particular structure (such as a spatial and polar organization) of the other molecule, so that the molecules of the pair have the property of binding specifically to each other. Examples of types of specific binding pairs (without any limitation thereto) are antigen-antibody, antibody-hapten, biotin-avidin, ligand-receptor (e.g., hormone receptor, peptide-receptor, enzyme-receptor), carbohydrate-protein, carbohydrate-lipid, lectin-carbohydrate, nucleic acid-nucleic acid (such as oligonucleotide-oligonucleotide).

"Nucleic acid" refers to a deoxyribonucleotide polymer (DNA) or ribonucleotide polymer (RNA) in either single- or double-stranded form, and also encompasses synthetically produced analogs that can function in a similar manner as naturally occurring nucleic acids. While natural nucleic acids have a phosphate backbone, artificial nucleic acids may contain other types of backbones, nucleotides or bases. These include, for instance, peptide nucleic acids (PNAs) as described in, e.g., U.S. Pat. No. 5,948,902 and the references cited therein; pyranosyl nucleic acids (p-NAs) as described in, e.g., WO 99/15540 (p-RNAs), WO 99/15539 (p-RNAs), and WO 00/11011 (p-DNAs); locked nucleic acids (LNAs), as described in, e.g., U.S. Pat. No. 6,316,198; and phosphothionates and other variants of the phosphate backbone of native nucleic acids.

The term "receptor" or "antiligand" refers to any compound or composition capable of recognizing a particular spatial and polar organization of a molecule, e.g., epitopic or determinant site. Illustrative receptors include naturally occurring receptors, e.g., thyroxine binding globulin, antibodies, enzymes, Fab fragments, lectins, nucleic acids, nucleic acid aptamers, avidin, protein A, barsar, complement component C1q, and the like. Avidin is intended to include egg white avidin and biotin binding proteins from other sources, such as streptavidin.

"Oligonucleotide" refers to single stranded nucleotide multimers of from about 5 to about 100 nucleotides.

"Antibody" refers to a polypeptide substantially encoded by an immunoglobulin gene or immunoglobulin genes, or fragments thereof. The recognized immunoglobulin genes include the kappa, lambda, alpha, gamma, delta, epsilon, and mu constant regions, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. Typically, an antibody is an immunoglobulin having an area on its surface or in a cavity that specifically binds to and is thereby defined as complementary with a particular spatial and polar organization of another molecule. The antibody can be polyclonal or monoclonal. Antibodies may include a complete immunoglobulin or fragments thereof. Fragments thereof may include Fab, Fv and F(ab')2, Fab', and the like. Antibodies may also include chimeric antibodies made by recombinant methods.

"Cell surface analyte" as used herein refers to a molecule or receptor situated on the external surface of a cell. The cell surface analyte may be an antigen having a specific immune reaction. Cell surface antigens may, for example, consist of carbohydrates, lipids or proteins.

"Sample" as used herein refers to any liquid sample that may contain cells either from cell culture or isolated from an organism, an organ, a body liquid or a tissue. The fluid sample can be used as obtained directly from the source or following a pretreatment so as to modify its character. Such samples can include human, animal or man-made samples. The sample can be prepared in any convenient medium which does not interfere with the assay. The fluid sample can be derived from any source, such as a physiological fluid, including blood, serum, plasma, saliva, sputum, ocular lens fluid, sweat, urine, milk, ascites fluid, mucous, synovial fluid, peritoneal fluid, transdermal exudates, pharyngeal exudates, bronchoalveolar lavage, tracheal aspirations, cerebrospinal fluid, semen, cervical mucus, vaginal or urethral secretions, amniotic fluid, and the like. Herein, fluid homogenates of cellular tissues such as, for example, hair, skin and nail scrapings, meat extracts and skins of fruits and nuts are also considered biological fluids. Pretreatment may involve preparing plasma from blood, diluting viscous fluids, and the like. Methods of treatment can involve filtration, distillation, separation, concentration, inactivation of interfering components, and the addition of reagents. Alternatively, the fluid sample may be a growth medium into which a biological sample containing a suspected microorganism may have been placed and incubated. Besides physiological fluids, other samples can be used such as water, food products, soil extracts, and the like for the performance of industrial, environmental, or food production assays as well as diagnostic assays. In addition, a solid material suspected of containing the analyte can be used as the test sample once it is modified to form a liquid medium or to release the analyte. The selection and pretreatment of biological, industrial, and environmental samples prior to testing is well known in the art and need not be described further. Exemplary cell types that may be of interest for use in the assay include: bacterial cells, liver cells, gastrointestinal cells, epithelial cells, endothelial cells, kidney cells, cancer cells, blood cells, stem cells, bone cells, smooth muscle cells, striated muscle cells, cardiac muscle cells, and nerve cells. Blood cells include, e.g., leukocytes, such as neutrophils, lymphocytes, monocytes, eosinophils, basophils, macrophages.

"Intracellular analyte" as used herein refers to a molecule situated inside a cell. The intracellular analyte may be an antigen having a specific immune reaction. Intracellularly bound analytes may, for example, consist of carbohydrates, lipids or proteins, ATP and nucleic acids.

Generally speaking, the systems described herein are directed to diagnostic assays and devices involving the capture, detection and identification of cells on a solid phase array. As required, embodiments of the present invention are disclosed herein. However, the disclosed embodiments are merely exemplary, and it should be understood that the invention may be embodied in many various and alternative forms. The Figures are not to scale and some features may be exaggerated or minimized to show details of particular elements while related elements may have been eliminated to prevent obscuring novel aspects. Therefore, specific structural and functional details disclosed herein are not to be interpreted as limiting but merely as a basis for the claims and as a representative basis for teaching one skilled in the art to variously employ the present invention. For purposes of teaching and not limitation, the illustrated embodiments are directed to diagnostic assays and devices involving the capture, detection and identification of cells on a solid phase array.

Embodiments as disclosed herein provide methods and devices for the multiplexed detection of cells in a solid phase, array-based assay format. In a first embodiment, a method is provided for the detection of intracellular analyte.

In the first step, a liquid sample that may contain cells is contacted with a solid support that comprises an immobilization region comprising adherent material for capturing the cells onto the solid support. The adherent material is preferably provided in an array of immobilization regions, such as spots or lines. The adherent material may comprise receptors that specifically binds with cell surface antigens, or may comprise a material that non-specifically binds to the surface of the cells. Each immobilization region in the array is employed to perform a spatially multiplexed assay. The sample is incubated while contacting the solid support, during which time cells present in the sample may bind with the adherent material forming the array. Alternatively, the sample may contact the solid support in microfluidic flow cell, in which sample is flowed over the solid support in a controlled manner to promote the capture of cells.

In a second step, the solid support is preferably washed to remove unbound and non-specifically bound cells, proteins, and other molecules that could otherwise generate artifacts, background, noise and/or cross-reactions.

In a third step, intracellular analyte is released from cells bound to the solid support by the application of an electric field of sufficient strength to cause electroporation or electrolysis of the bound cells. This step of in-situ electroporation or electro-lysis causes intracellular analyte released from a given cell to be initially concentrated in the region directly above the immobilization region to which the cell is bound. Electric-field-mediated lysis does not result in appreciable fluid flow or mixing, and therefore enables the release of intracellular components to be initially confined to the local area proximal to the immobilization region for a time duration dictated primarily by diffusion alone. Moreover, unlike chemical lysis methods, the use of an electric field enables the introduction of detection reagents prior to lysis, so that intracellular analyte may immediately contact detection reagents once released from the cell. This key aspect of the present lysis method allows for spatially-resolved detection of multiplexed assays in an array format.

A fourth step involves a detection step, in which one or more detector reagents are employed to generate a signal indicative of the presence of a particular intracellular analyte. The signal is locally generated in the vicinity of each immobilization region in the array, and the signal produced at each immobilization region in the array is detected. Accordingly, with each immobilization region in the array representing a distinct multiplexed assay, the signal from each assay is obtained by a detection system capable of spatially resolving the signals from the spots in the array.

Microfluidic Device for Concentration, Lysis and Detection

According to a preferred embodiment, the cellular analyte is concentrated in a first zone of a microfluidic channel, and then flowed under laminar flow conditions within proximity of an adherent surface provided in a second zone downstream of the first zone. Preferably, the cellular analyte is captured via specific binding forces to the adherent surface.

The cellular analyte is preferably a surface bound membrane structure such as a biological cell, and more preferably, bacteria and/or fungi. In a selected embodiment, part of the cellular contents are released by subjecting the cells to local pulsed electrical fields which open pores on the cell membrane. Specific molecules in the released cellular content may react with appropriate reagents and the presence of cells is detected via resulting optical or electrical signals. The device may form a component of a low, medium or high throughput automated analyzer system, and may optionally be configured as a disposable device. Preferably, the device is a consumable utilized in a separate electronic device, thereby providing a system for controlling the forces exerted on a cell primarily for the purpose of optimum cell retention regardless of the ionic composition of the aqueous sample.

In the preferred embodiment the device has a microfluidic structure comprising a longitudinal channel with dimensions adapted to support laminar flow therein. FIG. 1 shows a non-limiting example of the device, 1. It has a thin flow channel 14 which is defined by the base plate 12 and top plate 13 separated by a thin spacer with the channel cut from it. Typically, the spacer is made of a dielectric material which is slightly deformable under an applied clamping pressure. The spacer thus defines the side walls of the channel, provides the fluid seal, and electrically insulates the top and bottom plates from each other. While the channel is disclosed in FIG. 1 as being formed between two plates and laterally bound by a spacer layer, those skilled in the art will readily appreciate that a wide variety of channel geometries and assemblies are envisioned by the present embodiments. In a further non-limiting example, the channel may be formed as a recess within a substrate, where a top plate defines the top channel wall, and the recess defines both the lower channel wall and the lateral channel walls.

The channel includes an inlet 10 through which fluids may be introduced such as the fluid sample to be analyzed and other liquids which may be required for channel washing or detection of the cellular contents. The device is also equipped with an outlet 11 that can be in fluid communication with a collecting means such as a waste chamber, or, for example with an absorbent pad. Flow along the channel is provided by means of a pressure differential between inlet and outlet ports.

In one embodiment, the pressure differential may be generated by a pump means such as external pump that is interfaced to the device through fluidic fittings known in the art, such as tubing and sealing fittings. While the sample may be made to flow directly from the inlet to the outlet port of the device, alternative embodiments may be used in which the sample is re-circulated within the channel, thereby increasing the likelihood that cellular analyte will be captured by adherent material in the second zone of the device. In yet another embodiment, the pump means may be configured to produce an oscillatory flow of the sample in a longitudinal direction to increase the binding probability. In another embodiment, fluid may be introduced into the sample through a manual or automated pipettor configured to inject sample and/or other reagents or buffers into the inlet port.

The working section of the flow channel 14 is divided into two zones. The first zone is referred to as the "concentration zone" and has dimensions adapted to produce laminar flow. In a non-limiting example, dimensions H, W and $L_I$ may be selected to be on the order of approximately $0.1 \times 5 \times 10$ mm$^3$. Two electrodes 15 and 16, respectively at the inner sides of the plates 12 and 13, are intended for inducing an electric field across the zone. The voltage is preferably applied by an external voltage source, which is preferably electrically connected to external contact pads on the device that are themselves connected to the plates 12 and 13.

The time dependent electric field exerts an effective force on cells, provided that they comprise a surface charge, and carries them to a thin region at the immediate vicinity of the anodic electrode 15. Details of the time dependent pulses are provided below. The second zone may also be referred to as "reaction zone" and contains an adherent material for capturing the concentrated analyte. In a non-limiting example, the second zone may have a longitudinal dimension $L_{II}$ in the range of 10 mm.

As described above, the second zone contains an adherent material, which preferably selectively binds to the cells. The adherent material is preferably provided in a horizontal stripe that is approximately perpendicular to the direction of fluid flow within the channel. In this manner, cells concentrated to the region just above the channel surface flows over the adherent material and the binding capability of the device is enhanced. Preferably, the adherent material is selective and provided in the form of an array 19 of stripes have been created to bind to more than one type of cells. Those skilled in the art will understand that a wide range of other geometries of arrayed immobilization regions and stripes are possible within the scope of the present invention. In one non-limiting example, the array may be a regular array of spots. The arrayed adherent material may further comprise additional molecular components to improve the performance of the adherent material, for example, excipients for non-specific blocking, shelf life stability, and hydrogel materials for improved porosity and/or binding capacity.

In a preferred embodiment, each array element is a geometrically well defined area over which an adherent material (e.g. capture ligands specific to a class of analyte) have been immobilized. As the cells, concentrated at the lower extremity of the channel, slowly move over the array of binding elements, they may bind with the adherent material and become captured onto the solid phase. In a preferred embodiment, at least a portion of the channel is transparent within the second zone, thereby enabling the direct optical probing of bound cells. For example, the presence of cells bound to the adherent material may be determined by many optical methods, such as, but not limited to, light scattering, fluorescence, chemiluminescence, imaging, and surface plasmon resonance.

In a preferred embodiment, two electrodes 17 and 18 are additionally provided at the inner sides of the plates 12 and 13, and are intended for inducing an electric field across the second zone for the electroporation or electro-lysis of captured membrane bound or cellular analyte. The adherent material (either as a single line or array) is provided on the inner surface of one of the electrodes (the electrode 17). Applying a brief and large potential difference between the two electrodes 17 and 18 electroporates cells and depending on the magnitude and duration of the resulting electric field some molecules inside the cell are released. These can be used for detecting the cell's presence. Preferably, one of the electrodes 17 and 18 is transparent, thereby enabling the direct optical detection of a signal from the interaction of the released intercellular material with one or more detection reagents flowed through the channel.

Concentration Module

The section of device 1 that constitutes the first zone is referred to as the "concentration module". It is intended for separation of charged cells based on application of a non-Faradaic electric field (i.e. no charge is transported across the double layer formed at the channel walls). When a sample containing charged cells (for example, bacteria) is injected through the inlet 10 into the device, it develops a uniform Poiseuille flow in longitudinal direction by the time it reaches to the concentration zone. There, the charged cells are subjected to a transverse electric field and is concentrated to one side of the channel under an electrophoretic force.

As mentioned above, in a preferred embodiment, the charged cells are microorganisms such as bacteria or fungi. At physiological pH (5-7), most microorganisms are negatively charged because the number of carboxyl and phosphate groups exceeds the number of amino groups at the cell surface. As charged particles, these cells experience an attractive force towards the anode 15, henceforth termed the "accumulation wall". As the cells approach the wall, their overall motion is halted by various repulsive forces, lift forces and diffusive forces associated with Brownian motion and are held at a small distance away from the wall. At regions close to the exit of the concentration zone a Guassian-type concentration profile of cells is formed in the proximity of the accumulation wall. The cells then slowly travel to the reaction zone at the velocity associated with the flow at the equilibrium distance from the wall.

The main challenge for the successful operation of the concentration module is establishing a transverse electric field with sufficient strength in the central region of the channel. It is well known that the application of a constant electric field in a channel containing an aqueous solution results in formation of electric double layers near the electrodes and in some instances as much as 99% of the potential drop occurs across the double layers. Accordingly, the actual electric field experienced by the charged cellular analyte, referred to as the "effective field", is only a small fraction of the nominally applied field and the bulk of the liquid in the channel is shielded from the electrodes by polarization layers of ions and water molecules on the electrode surfaces.

Unfortunately, clinical samples generally have high ionic strengths. For example, a common culture medium tryptic soy broth includes 5 g/L of sodium chloride and 2.5 g/L of dipotassium phosphate. These salts give rise to an ionic strength of about 100 mM. If such a solution is introduced into a channel with at least one blocking electrodes connected to DC power supply, the non-Faradaic electric potential will drop by 37% at a distance of about 1 nm from the electrode. This distance is the Debye length, $\lambda_D$, related to the ionic strength I by the following relation;

$$\lambda_D = 0.304/\sqrt{I}$$

where I and $\lambda_D$ have the units of mole/L and nm, respectively.

Application of an electric potential difference between two unblocked electrodes separated by an electrolytic solution can result in electrochemical reactions at the electrode-electrolyte interface if the applied voltage exceeds a threshold value. In that case gas bubbles are generated at the electrodes due to electrolysis of water. The gas formation can rapidly obstruct the channel leading to electrophoretic failure. In addition, the pressure increase in the channel might cause mechanical damage of the module. The amount of lateral electric field that can be applied is therefore limited by the restriction that it should not result in generation of gases in amounts exceeding the solubility limit.

A common approach in the prior art involves suppressing the generation of oxygen and hydrogen bubbles by adding a redox-couple to the sample flowing along the electrodes. As an example, quinhydrone, which is a complex between hydroquinone ($H_2Q$) acting as an electron donor and p-benzoquinone (Q) acting as an electron acceptor, can be added to the flow streams. Instead of water oxidation and reduction that generates oxygen and hydrogen, now $H_2Q$ is oxidized and Q is reduced without any bubble generation. Obviously, this method complicates sample introduction and contradicts the goal of performing a low cost and rapid assay.

In contrast to known methods, both of the foretold issues, i.e. gas bubble formation and the field shielding, may be alleviated by including at least one electrical insulating layer to prevent a Faradaic current from flowing in the channel. The generation of gas bubbles is avoided by insulating the anode from the sample with a thin layer of dielectric coating, which serves to eliminate any charge transfer processes from occurring across the electrode-electrolyte boundary. In another embodiment of the invention, the electrodes may be non-blocking, and the generation of a Faradaic current may be suppressed by maintaining the applied voltage below the threshold voltage.

Thus in a preferred embodiment of the invention, the device is non-Faradaic and comprises at least one blocking electrode, and the shielding of the electric field at central parts of the channel is partially avoided by applying the driving voltage in two stages. In the first step, termed as on-time, a potential difference is rapidly created between the two electrodes and is maintained over a time period of $t_{on}$. Over this time period the double layer is being developed on the electrode-electrolyte interface and field strength within the channel is still appreciable. In the second step, the applied electric field is zero or slightly negative for time $t_{off}$, termed as off-time. This time is sufficiently long to allow the smaller ions, such as $Cl^-$, to diffuse back and rebuild their uniform distribution. On the other hand, $t_{off}$ should be sufficiently short that the average diffusive displacement of the cells during off-time does not exceed (preferably does not amount to more than a few percent of) the electrophoretic displacement they received during on-time. As will be shown below, the much higher diffusivity of ions relative to cells makes this possible.

Figure 2:
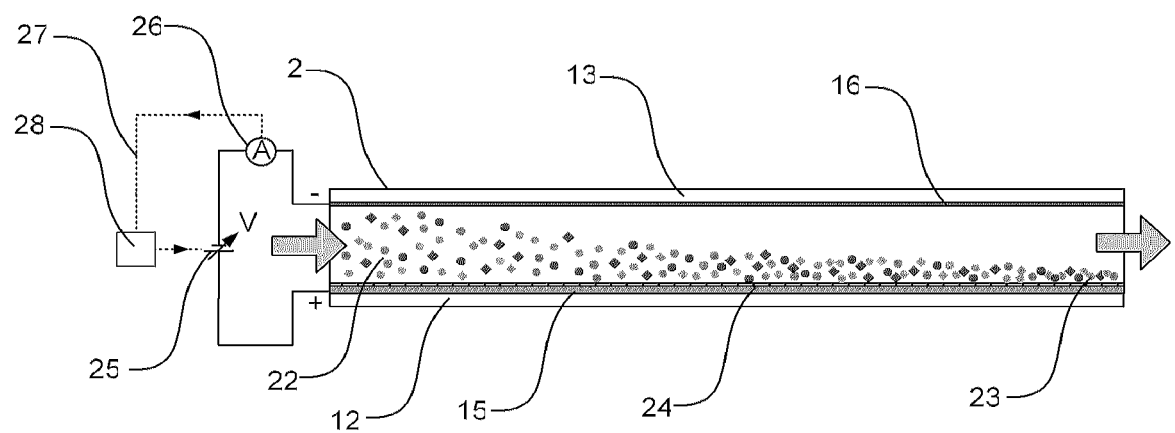
FIG. 2 shows a schematic cross-sectional view parallel to the flow of the concentration zone.

The construction and operation of an exemplary but non-limiting example of the concentration module is now described by referring to its schematic cross-sectional view parallel to the flow that is illustrated in FIG. 2. In the preferred embodiment, the transparent electrode 16 is commonly prepared by chemically bonding a conductive metallic oxide coating to an optically transparent plate such as glass (13). The preferred oxide layer is a thin layer of ITO (Indium tin oxide), approximately 100 nm thick. The transparency of the electrode is essential for accessing the signal in the reaction zone if the reactions devised for detecting the cellular contents have been selected to generate optical signals. As it is known in the prior art, other transparent or partially transparent conductive layers, such as thin metallic films, can be used instead of the ITO layer.

The electrode 15 is preferably mounted on a base plate 12. This electrode preferably has a dielectric surface layer, 24 at the channel interface. The dielectric layer may be prepared by coating the plate with a thin layer of materials such as polystyrene. In the preferred embodiment, the conductive electrode 15 and the base plate 12 are aluminum and the dielectric coating 24 is aluminum oxide ($Al_2O_3$). The surface of aluminum oxide is preferably modified to create hydroxyl groups followed by coating with a heterobifunctional silane layer, creating functional groups to interact covalently with the capture ligands. In applications requiring long exposure to $Cl^-$ the oxide layer may not provide enough corrosion protection. In this case the observation by B. F. Shew et al (*J. Electrochem. Soc.* 138: 3288 (1991)) can be utilized in preparation of the electrode. The addition of quite small quantities (5 mol % and less) of transition metals (e.g., Ta, Mo, and W) to Al can reduce the rate of corrosion of Al by up to about 100 times, and the time to breakdown under constant electric field across the protective oxide layer may be increased by about 10 times.

Using an external voltage source, 25, a potential difference is applied between the two electrodes, 15 and 16, with the bottom electrode having a positive potential with respect to the top electrode. The output of the voltage source 25 is preferably a high frequency train of pulses and the pulses are preferably substantially square. The frequency, the amplitude and the pulse shape of the applied electric waveform may be predetermined based on known properties of the sample liquid, or may be selected according to the feedback based on the current monitored by the meter 26. Those skilled in the art will appreciate that the waveform may be varied in order to optimize the performance of the device.

As schematically illustrated in the figure, the inflow 22 has a substantially uniform distribution of the suspended cells. As a result of the concentrating action of the module in the outflow 23 the cells are localized close to the anode surface. The liquid convection slowly carries them to the reaction zone.

The basic structure of the concentration module is analogous to the structure of a polarized electrolytic capacitor. In such capacitors the aluminum oxide ($Al_2O_3$) dielectric layer is formed by electrochemically oxidizing the aluminum. In order to increase the effective surface by as much as 100 times, and so increase the capacitance per unit nominal area, the electrode is etched with a dense network of microscopic tunnels. The thickness of the dielectric layer is determined by the applied voltage during the electrochemical forming (anodizing) process and is often chosen to be 2 nm per each volt that can be safely applied on the electrode. Since the required voltage at the concentration module does not exceed a couple of volts in many applications, naturally occurring $Al_2O_3$ layer (thickness about 5 nm) may be sufficient.

Circuit Model of Electrical Concentration Module

Figure 3:
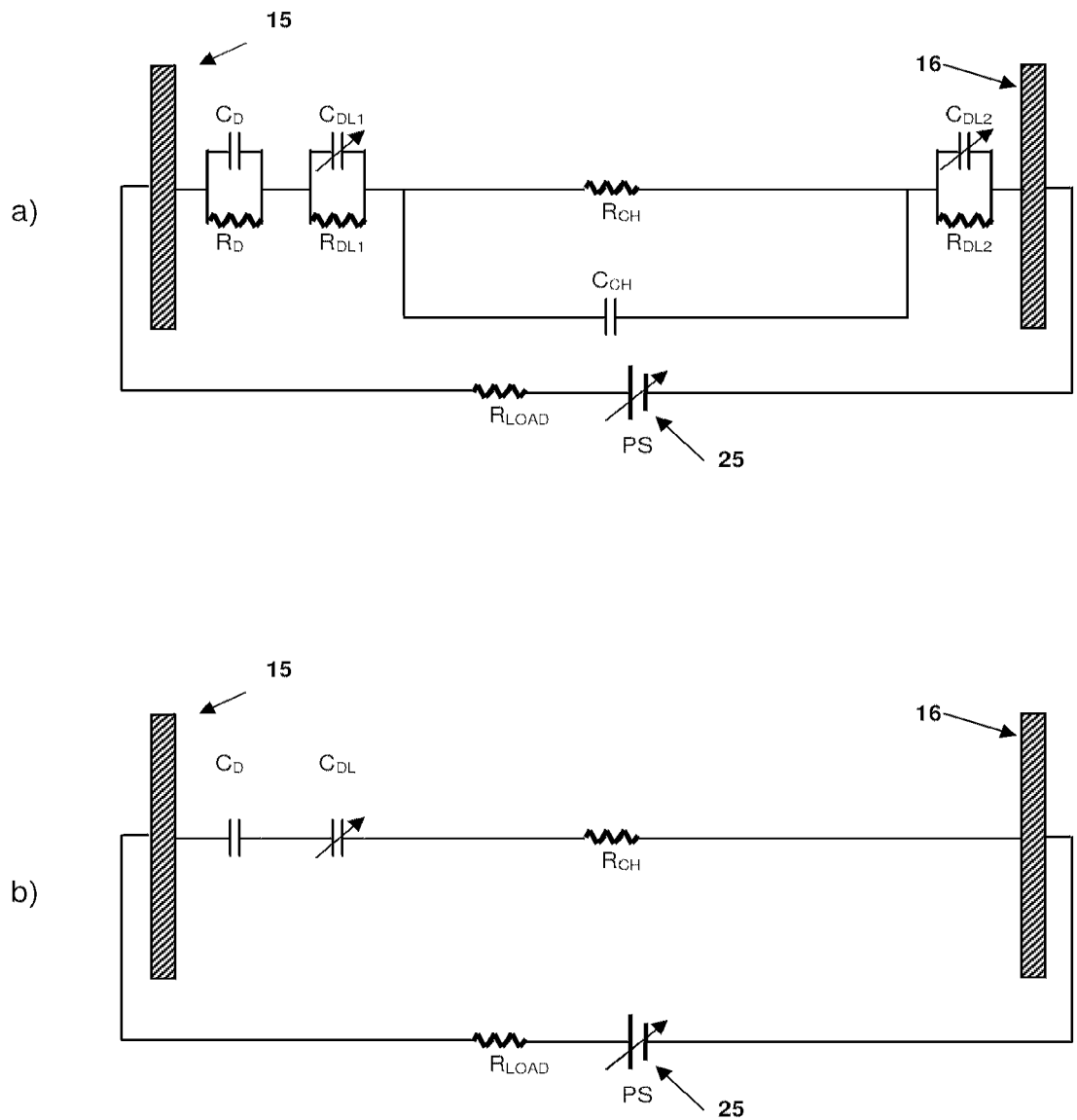
FIG. 3 shows the equivalent circuit model for the concentration module.

The concentration module can be modeled by the equivalent electrical circuit presented in FIG. 3a. The capacitance $C_{DL1}$ and $C_{DL2}$ correspond to the dynamic double-layer capacitances at the interfaces of dielectric layer 24 and electrode 16 respectively with the liquid in the channel. $R_{DL1}$ and $R_{DL2}$ are the parallel resistances corresponding to leakage current in the two capacitors. In general, values of $C_{DL}$ for flat metal surfaces fall in the range 5-50 $\mu F/cm^2$ depending on the type of metal, ionic strength and composition of the solution, surface roughness, temperature and voltage.

Capacitance $C_{DE}$ is the capacitance of the dielectric layer whose value depends on the layer thickness and the effective area of the electrode. For example, roughness of the surface can increase capacitance by a factor as high as 1000. Resistance $R_{DE}$ is the equivalent parallel resistance of the dielectric layer and accounts for leakage current in the capacitor. It decreases with increasing capacitance, temperature and voltage. Typical values for $R_{DE}$ are on the order of $100/C_{DE}$ M$\Omega$ with $C_{DE}$ in $\mu F$.

$R_{CH}$ represents the bulk solution resistance and $C_{CH}$ the bulk capacitance. The value of $C_{CH}$ is so small that it can be approximated with open circuit. For a channel with a width of 100 $\mu m$, the resistance $R_{CH}$ is about 100 $\Omega/cm^2$ for an ionic strength of 1 mM.

$R_{LOAD}$ is the sum of the power supply output resistance and the input resistance of the electrodes. All the electrical parameter values, with the exception of $R_{LOAD}$, $R_{DE}$ and $C_{DE}$ are dependent on the ionic strength of the carrier solution. The load resistance modifies the voltage division among the circuit components and becomes particularly important at higher ionic strengths.

Considering the typical values of the electrical parameters, the equivalent circuit can be simplified as presented in FIG. 3b. The resistances $R_{DE}$, $R_{DL1}$ and $R_{DL2}$ are sufficiently large that they can be approximated as open and the two double layer capacitances have been combined in series as $C_{DL}$. The double layer charging time, according to this circuit model, is given by $$\tau_c(R_{LOAD}+R_{CH})(C_{DE}C_{DL}/(C_{DE}+C_{DL})) \quad (2)$$

Thus, the period $t_{on}$ over which the potential difference is maintained between the electrodes should be chosen to be in the order of $\tau_C$. Bazant et al (Physical Review E 70, 021506 (2004)) have suggested that the primary time scale for charge relaxation is given by $$\tau_D=\lambda_D^2/D_{ion}, \quad (3)$$

were $D_{ion}$ is the diffusivity coefficient of the ions and $\lambda_D$ is given by relation (1). Preferably, $t_{off}$ the period over which the potential difference between the electrodes is brought to zero, is chosen to be longer than $\tau_D$.

As it can be easily remarked both characteristic times of the concentration module ($\tau_c$ and $\tau_D$ of equations 2 and 3) depend on the ionic strength of the aqueous solution. This implies that optimum values of $t_{on}$ and $t_{off}$ will vary for samples with different ionic strengths. While these value can be chosen empirically for a given sample type, or predicted if the sample ionic strength is known or can be measured, a preferred embodiment, employs a feedback loop, shown in FIG. 2 at 27, comprising a current meter 26 and the controller unit 28.

In one embodiment, depending on the current measurement at some points in time the lumped circuit parameters of the module can be estimated and optimum values of $t_{on}$ and $t_{off}$ determined and applied. This control scheme is based on the fact that the current flow is an indicator of the effective electric field experienced by cells in the channel. According to M. Marescaux et al. (PHYSICAL REVIEW E 79, 011502 (2009)), there are two contributions to the current flow. Double layer charging is initially the dominant phenomenon, resulting in an exponentially decreasing transient current. At the second stage, termed as "delayed buildup", near the double layer, the concentration of positive and negative charges becomes lower than in the bulk. As a result, positive and negative charges diffuse toward the electrodes. The readjustment of the double layer leads to a measurable current. This transient current is negligible during the initial double layer charging, but it becomes dominant at longer times because it decreases more slowly than an exponential decay. The applied potential difference across the two electrodes should be turned off before the onset of the "delayed buildup" as by then the electric field will already be shielded from the channel center.

In another embodiment, the feedback means may comprise the measurement of a circuit parameter, such as the current, and the time $t_{on}$ may be determined to be the time interval following the initial application of the electric field and the time at which the measured current falls below a pre-determined threshold. In one embodiment, the threshold may be a pre-selected fraction of the current measured when the electric field is initially applied.

In a preferred embodiment, the threshold is determined by applying an initial series of pulses to the electrodes and measuring the resulting current, and fitting the measured current to a known function. For example, the measured current may be fitted to an exponentially decaying function, and the threshold may be approximately equal to the current measured at a time approximately equal to a fitted time constant.

Without intending to be limited by theory, the effectiveness of the concentration module is believed to be dependent on the fact that while electrophoretic mobilities of non-motile cells and smaller ions are numerically of the similar order of magnitude, their diffusivity coefficients vastly differ. In order to illustrate this principle, a generic example is provided.

We consider an electrolytic sample containing a suspension of non-motile bacteria having spherical shapes with a radius of 1 μm that flows into a concentration module. The channel height, H, is taken to be 100 μm. The diffusivity coefficient and electrophoretic mobility of the bacteria is estimated to be $D_{cell}=2.2\times10^{-9}$ cm$^2$/s and $\mu_{cell}=2.0\times10^{-4}$ (cm/s)/(V/cm), respectively. Square pulses with $t_{on}=0.5$ ms and $t_{off}=2$ ms are applied to the electrodes. The amplitude of the pulses are adjusted such that the effective field during the "on" time is $E_{eff}=100$ V/cm. The average lateral displacement of the bacteria during on-time $\Delta y_{cell}=\mu_{cell}E_{eff}t_{on}=0.1$ μm. During the off-time the cell randomly diffuse over an average length of $\delta_{cell}=\sqrt{D_{cell}t_{off}}=2.1\times10^{-2}$ μm. The ratio $\delta_{cell}/\Delta y_{cell}$ is calculated to be 21%. Its smallness indicates that the diffusion does not severely disturb the trajectory of the bacteria that will reach the collecting wall after $H/(2\Delta y_{cell})=500$ cycles, if it had started from the channel center. On the other hand, for a Cl$^-$ ion with diffusivity coefficient and mobility of $D_{ion}=1.86\times10^{-5}$ cm$^2$/s and $\mu_{ion}=8.0\times10^{-4}$ (cm/s)/(V/cm) the corresponding displacements are $\Delta y_{ion}=0.4$ μm and $\delta_{ion}=1.93$ μm. Then, $\delta_{ion}/\Delta y_{ion}=480\%$, indicating that when the external field is switched off, the ions relax to a uniform density distribution, driven by diffusion.

In selected cases, the motility of bacteria can affect the performance of the concentration module. In the absence of a force field and in a large container motile cells move by propelling themselves by means of long hairlike flagella with a swimming pattern that resembles a three-dimensional random walk. The usual Fickian diffusion can be used to describe their random motility as is done, for example, by P. Lewus, R. M. Ford (Biotechnology and Biosensing 75 292 (2001)) who showed that the motion of *E. coli* AW405 is similar to a particle with an diffusion rate of $3\times10^{-6}$ cm$^2$/s. This value is close to the diffusivity coefficient of small ions. However, there are two reasons that suggest that, in the presence of cell motility, the concentration module should remain effective. In the presence of electric field bacteria cells align themselves along the electric field and will migrate toward one electrode depending on the nature of the cell surface, known as galvanotaxis. As a result of galvanotaxis the motion of the cells is thus restricted to the lateral direction. Also, when a bacteria cell collides with the channel surface it tends to swim parallel to the surface and therefore will accumulate near the surface as described by G. Li and J. X. Tang PRL 103, 078101 (2009). The pulsing nature of the applied electric field will increases the number of collisions to enhance this effect.

The concentration module can operate over a wide range of ionic strengths. However, high ionic strength lowers the performance of the module for three reasons: 1) the electrophoretic mobilities of the cells appreciably reduce as the ionic strength increases, which requires application of higher voltages for efficient concentration; 2) high ionic strengths are associated with shorter charging times, thus requiring shorter $t_{on}$ as a result of which the duty cycle, defined as $t_{on}/(t_{on}+t_{off})$, is reduced; and 3) The channel resistance, $R_{CH}$, is inversely proportional to the ionic strength, and the lower this resistance becomes the more heat is generated in the electrodes and the channel, which may have deteriorating effects on the cells. Therefore, reducing the ionic strength generally results in the improved performance of the concentration module. The task of ion reduction in the sample can be performed by the sample pre-treatment module that may be integrated in the sample inlet 10 of the device (see FIG. 1).

Sample Pre-Treatment

Figure 4:
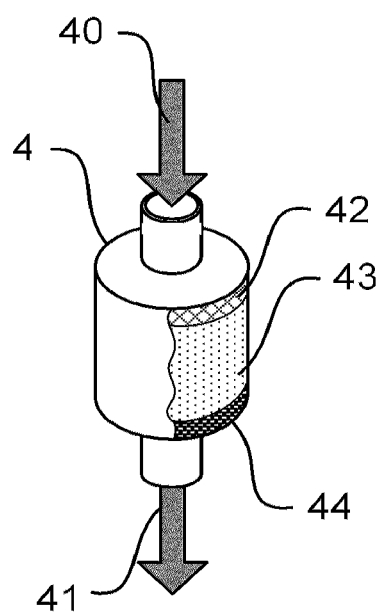
FIG. 4 shows the sample pre-treatment module.

FIG. 4 shows an example of a sample pre-treatment filter according to a preferred embodiment of the invention. The sample pre-treatment module, 4, consists of inlet 40, outlet 41, pre-filter, 42, packed ion exchange resins, 43, and a filter, 44. The pre-filter 42 excludes large particles such as cationic exchange resins and non-ionic adsorbing resins used in some samples such as the culture media of the Becton Dickinson system. The ion exchange resins (43) comprising mixed cationic and anionic resins serve to de-ionize the sample and to capture smaller ionic particles (for example, activated charcoal and fuller's earth powder, as employed in the culture media of bioMerieux). The filter 44 retains the ionic resins and bound ions and ionic particles to prevent them from entering the concentration module.

The pre-filter and the filter can be made of a non-woven polyalkylene porous material such as polypropylene, polyethylene or polytetrafluoroethylene porous frits with an appropriate pore size of about 35-125 μm suitable for retaining the resins and large particles. More preferably, the porous material is a chemical and thermal resistant material such as high density polyethylene. A pre-filter and a filter may be present at the respective ends of a tube such as heat shrinkable low density polyethylene tubing and ion exchange resins will be packed in between. Preferably, a pre-filter, a filter and a tubing material will be a hydrophilic type or coated with a hydrophilic polymer. Hydrophilic high density polyethylene porous sheets to make pre-filters and filters, and low density polyethylene tubing materials are widely available from commercial sources.

To de-ionize the ions and ionic particles, mixed H$^+$ form cation exchange resin and OH$^-$ form anion resin may be used. Na$^+$ in the medium binds to the cation resin in exchange of H$^+$ and Cl$^-$ binds to the anion resin in exchange of OH$^-$. Removed H$^+$ and OH$^-$ form H$_2$O molecules. This method is widely applied in water deionization. Preferably, microporous gel resins with the pore size larger than the size of bacteria or other cellular analyte of interest are be used. In addition, as negatively charged bacteria can still bind to the surface of the anionic resin and nonspecifically bind to the surface of the resins, both types of resins will be treated with a non-ionic surfactant such as TritonX-100. Examples of mixed resins are Amberlite MB-150 from Rohm & Hass and Dowex-Marathon MR-3 from Dow Chemicals with particle sizes ranging from 500-700 μm.

Reaction Zone

Figure 5:
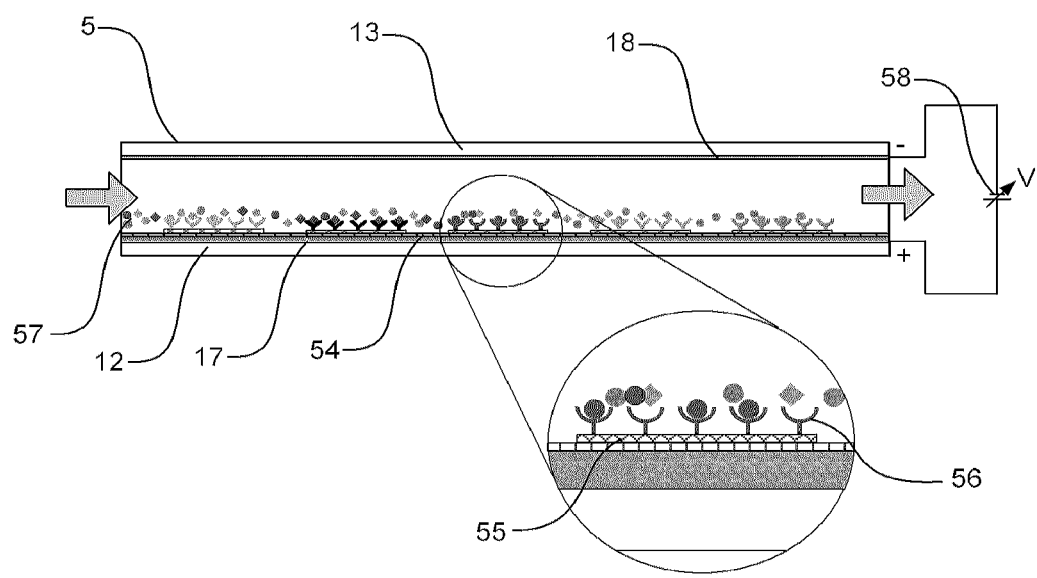
FIG. 5 shows a schematic cross-sectional view parallel to the flow of the reaction zone.

A cross section of the second zone is schematically presented in FIG. 5. This section of the device is known as the reaction module. It can be understood to be an extension of the concentration module and during the sample concentration stage the optional additional electrode pair 18 and 17, like the two electrodes 16 and 15 of the concentration module, may be driven by the power supply 25 of FIG. 2 to further assist in the sample concentration. The inflow 57 is passed along from the concentration zone by fluid convection.

The cells, which have been localized at the lower extremity of the flow, do not diffuse into the central region of the channel by the simultaneous action of the concentration mechanism in both concentration and reaction modules. This ensures more efficient cell-capture by the adherent material as the cells spend long times in the vicinity of the surface. In the zoomed section of the figure, a non-limiting embodiment is shown in which the adherent material comprises capture ligands which in this case have high affinity to the cells (e.g. high affinity to a selected class of cells represented by the black circles). In this embodiment, cells belonging to other classes will pass over to their respective immobilization regions without being retained. The capture ligands may be antibodies and are preferably immobilized by covalently binding to a layer of spacer molecules 55 at the immobilization regions.

While the aforementioned embodiments disclose a device comprising both a concentration zone and a reaction zone, it is to be understood that devices according to different embodiments may comprises either one or both of the concentration and reaction zones. For example, in one embodiment where the sample contains a relatively high concentration of cells, in which case a concentration step may not be necessary to bind a sufficient number of cells at the reaction zone, a device may comprise a reaction zone without a concentration zone.

The dielectric coating in the reaction zone 54 is preferably substantially thicker than its counterpart 24 in the concentration module. The large thickness ensures that the dielectric layer will be able to withstand the high strength of the electric field used during electroporation, as discussed below. In the preferred embodiment the layer is $Al_2O_3$ and the thickness is 2 nm per each volt to be applied on the electrode 17.

Once the entire sample has passed the channel and the cells are retained, an optional washing process can be performed by injecting a washing liquid into the channel. The flow carries away analyte that has been adhered on the channel surface. In the specific case of cells, they generally have little affinity to the non-adherent surface they may be displaced by shear force of the washing fluid. When more stringent washing is required, the washing action can be assisted by applying a weak repulsive electric force to the cells. This is done by reversing the polarity of the power supply 25 and applying a sequence of pulses to the electrodes.

Electro-Lysis and Detection

In a preferred embodiment, the reaction zone is employed for the electroporation or electrolysis of bound cell. The first step of the reaction stage is filling the channel with an electroporation liquid or buffer. The composition of this liquid depends on the nature of the intended reaction. For example, if the intention is to detect the presence of the cells via their ATP content, as further described below, the appropriate liquid should contain reagents necessary for initiating and driving the oxidation of luciferin under catalysis by luciferase followed by emission of light. A typical buffer may have the following composition: luciferase, D-luciferin, Tricine buffer pH 7.8, Magnesium sulfate, EDTA, DTT, BSA.

The release of desired cellular contents is accomplished by applying a strong electric field to the captured cells to make the cell membrane permeable to an outside medium. This method is known as electroporation. The electroporation of cell membrane can be reversible or irreversible, depending on the electric field strength.

Preferably, the electric field is made sufficiently high to cause irreversible breakdown of the cell wall. The irreversible breakdown of the membrane causes cell membranes to burst open, and then the osmotic pressure of the cytosol and the external medium become unbalanced and the cells are disrupted as a result of the overswelling. The irreversible electroporation is commonly known as cell lysis and is desirable in cases that the device is intended for the release of cellular molecules, such as ATP, nucleic acids and proteins.

Generally speaking, the internal field for electroporation or electro-lysis depends on many factors, including the size of and cell wall structure of the cell, the applied voltage, and the separation between the electrodes used to apply the field. The electric field strength required to achieve a trans-membrane potential of more than 1 V is about 1 kV/cm. Preferably, the applied voltage is selected to provide an internal electric field of at least 1 kV/cm, although this threshold is known to vary for different cell types and species. Depending on the applied field, electroporation can be permanent, or reversible.

The voltage may be applied in as DC or AC voltage, and may be continuous or pulsed. In a preferred embodiment, an AC voltage is applied to limit the formation of bubbles due to electrolysis. Preferably, the voltage is AC, has a frequency between 1 and about 10 MHz. In another preferred embodiment, the voltage is applied in one or more pulses, with each pulse lasting for at approximately 10 microseconds to 10 milliseconds. Those skilled in the art will readily appreciate that different combinations of voltage, frequency, pulse duration will be appropriate for different materials, geometries, and cell types.

In the previous art, two basic configurations have been suggested for performing electroporation or electro-lysis; axial-ohmic and transverse-ohmic. The axial-ohmic configuration has been utilized in the microfluidic devices (e.g. U.S. Pat. No. 6,287,831, and Wang et al., Biosensors and Bioelectronics 22:582-588, 2006). The required field is generated by the voltage drop as an electric current passes through a high resistance aqueous medium containing a suspension of cells. An electrical field is then established along the length of the device by inserting two wires into the sample inlet and outlet.

The transverse-ohmic configuration is utilized in commercial electroporation vessels (e.g. U.S. Pat. No. 6,074,605). In the basic form, the device includes a hollow housing substantially rectangular in shape. Two electrodes are inserted into the interior of the housing directly opposite one another, flush against the housing walls. The electroporation is performed by applying a voltage difference between the two electrodes. These configurations can be adopted in embodiments disclosed herein. Alternatively, for the embodiments for which the primary cell receptors are immobilized on a dielectric surface, the required field is generated by charging the capacitor formed by the two conductor electrodes, one attaching behind the dielectric surface and the other opposite to this surface. In this case the transit field is able to electro-lysing the cells.

While electrical lysis of cells in known, (e.g., *Bioelectrochemistry*, 2004, 64, 113-124. *Lab Chip*, 2005, 5, 23-29. *Anal. Bioanal. Chem.*, 2006, 385, 474-485. U.S. Pat. No. 7,418, 575), these methods teach that the cells should be suspended in a liquid medium and that a large electric field is required to be above the threshold strength in the entire volume of the medium. Devices based on such an approach have encountered challenges in achieving lysis due to the presence of the field shielding by the double layer formation.

In contrast, in the embodiments disclosed herein, the reaction module, the cells are surface bound. During the double layer charging process, while the field strength rapidly diminishes in the inner channel regions, it increases at the electrode boundary (*Phys. Rev. E* 70, 021506 (2004)). Therefore, relatively low potential differences are sufficient to provide high electric field strengths in the vicinity of the cells.

In order to illustrate the advantages of electroporation at the electrode surface, a non-limiting example is henceforth provided. Considering the case of a channel with a height (the dimension H in FIG. 1) of 100 μm, the intention is to lyse bacterial cells by irreversible electroporation. It has been reported that the required electrical fields are about 10 kV/cm. If the cells are suspended in the liquid, the power supply must deliver a potential difference of 100 V.

However, for the surface bound cells the voltage requirement can be substantially lowered. Without intending to be limited by theory, this finding may be interpreted within the context of a qualitative model of charge transport in an electric field developed by Beunis et al (Physical Review E, 78, 011502 (20008)). Immediately after the application of a voltage $V_A$ over the blocking electrodes at the reference time (t=0) a positive surface charge builds up near the negative electrode and a negative surface charge builds up near the positive electrode. Adjacent to the electrodes, space charge regions with thicknesses $\lambda_{SC}(t)$ occur where charges of one polarity are completely absent. For a sufficiently large value of the applied voltage drift is the dominant charge transport mechanism and diffusion can be neglected. Therefore, the speed at which the space charge regions grow is equal to the speed of charges in the bulk:

$$\frac{d\lambda_{SC}(t)}{dt} = \mu E_{bulk}, \quad (4)$$

where, $\mu$ is the mobility of ions (assumed to be the same for the positive and negative ions) and $E_{bulk}$ is the electric field in the bulk. Beunis et al. show that within reasonable approximations, the field in the space charge region, $E_{SC}$, can be calculated using the following equation:

$$E_{SC} = \sqrt{E_{bulk}^2 + \frac{4qnn}{\varepsilon\varepsilon_0}\left(x + \lambda_{SC} - \frac{H}{2}\right)E_{bulk}}, \quad (5)$$

where, q is the ionic charge, n is the average ionic density in the medium, $\varepsilon_0$ is the dielectric permittivity of vacuum and $\varepsilon$ is the relative dielectric constant of the medium, and x is measured from the center of the channel.

To estimate the internal electric field based on the above analysis, a microchannel having a height of 100 μm was filled with 170 μM NaCl solution, and a step voltage of amplitude $V_A$=1 V was applied to the channel electrodes. The measured current as a function of time (t in seconds) could be approximated by $$I(t) = \frac{I_0}{1 + (t/6.5 \times 10^{-4})^{1.2}}.$$

Accordingly, it was inferred that $$E_{bulk}(t) = \frac{V_A/H}{1 + (t/.5 \times 10^{-4})^{1.2}}.$$

Substituting this result in equation (4) with $\mu=7.15\times 10^{-8}$ m$^2$/V·s it was found that about 8 ms after the application of the external field, the width of the space charge region will be comparable to the typical size of a bacterial cell, i.e. $\lambda_{SC}$(t=8 ms)=1 μm. At this time the field strength in the center of the space charge region (0.5 μm from the electrode) reaches a magnitude of 1.5 kV/cm, which is 15 times higher than what was expected if the screening effect were not present.

The above analysis demonstrates that by selecting a dielectric layer having thickness and a dielectric constant such that the electric field drop occurs substantially within the space charge layer of the channel, an amplified electric field is obtained within the channel proximal to the dielectric layer. As noted above, a preferred thickness for the dielectric layer is in the range of about 10 to 100 nm, and a preferred dielectric constant of the dielectric layer is in the range of approximately 3 to 10, and more preferably above 10. Thus a separate high voltage power supply is not needed for the electroporation and a single low-cost power supply can drive the concentration, washing and electroporation processes. Moreover, due to the lower value of the required applied voltage, the thickness of the dielectric layer (preferably $Al_2O_3$) layer, necessary for electrode blocking, can be kept low and the reduction in the electrode charging time, and its associated problems, be avoided.

As described above, in one embodiment the adherent material comprises a cell-specific receptor, where cells bind specifically to the solid support directly via the specific binding of a cell surface with the receptor immobilized within an immobilization region. In a preferred embodiment, the adherent material that is provided for the binding of the cell to the solid support further includes immobilized secondary receptors that are specific to intracellular analyte released from the cells following the application of the electric field. The secondary receptors enable the capture of locally released intracellular analyte from a bound cell immediately following electroporation or electro-lysis. Preferably, the adherent material is provided in a spatial array, and the secondary receptors are provided within the array. The adherent material may be provided within an array of immobilization regions comprising primary receptors, with each immobilization region in the array comprising a receptor specific to a given type of cell or cells, and where each immobilization region further comprises a secondary receptor for detecting intracellular analyte post-lysis or post-electroporation. In another embodiment, the secondary receptors are provided within an immobilization region of the solid support adjacent to a given zone of adherent material.

The capture of cells by the adherent material and subsequent electroporation or electrolysis of cells on the solid support effectively concentrates the intracellular analyte near the secondary receptors, without the express need for thorough and efficient mixing. The subsequent addition of a detector reagent enables the detection and/or quantification of the presence of the intracellular analyte based on the spatial location of the signal in the array.

It is to be understood, however, that the present embodiment involving the capture of cells via the adherent material in the immobilization zone, the lysis of captured cells to release their intracellular contents, and the subsequent detection of the intracellular contents via the binding of the intracellular contents to secondary receptors provided in the immobilization region, is not limited to embodiments involving the electro-lysis or electroporation of bound cells. As such, the adherent material and secondary receptors need not be bound on an electrode and dielectric layer, but may be bound on any suitable solid support, as further described below. In one preferred embodiment, the adherent material and secondary receptors are provided within an immobilization region defined on a microplate well surface. To release the intracellular contents, any suitable lysis method may be employed, including, but not limited to, chemical lysis, mechanical lysis, and ultrasonic lysis.

It is to be further understood that while the preceding embodiments have been described within the context of the binding of cells to the solid support via the adherent material in order to disrupt the cell membrane (e.g. by electro-lysis or electroporation), the capture and/or concentration of the cells in the vicinity of the dielectric layer for subsequent electroporation or electro-lysis may be achieved by electric field mediated concentration alone, without the need for the adherent material within an immobilization zone. In such an embodiment, the preceding method of applying unipolar voltage pulses may be performed to concentrate the cells in the region proximal to the dielectric layer, preferably within or adjacent to the aforementioned space charge region. Once cells have been accumulated in this region under application of the electric field of the unipolar voltage pulses, a one or more voltage pulses with an amplitude sufficient for the disruption of the cellular membrane may be applied. Accordingly, cells in a cell-containing liquid sample may be concentrated proximal to the dielectric surface and electroporated and/or electro-lysed. In a preferred embodiment, the dielectric layer may comprise an immobilization region having thereon only secondary receptors for binding intracellular analyte released from the cells.

This unique aspect of embodiments disclosed herein enables highly sensitive detection of a wide range of intracellular analytes including proteins and nucleic acids. Furthermore, the local concentration of intracellular analyte in the spatial vicinity of the secondary receptors supports the detection of analyte with very low copy number, without resorting to complex mixing and concentration schemes. As will be shown in subsequent examples, these embodiments may be adapted to a wide range of assay platforms, and is particularly suited to automated analyzer systems that employ microfluidic cartridges.

In a preferred embodiment, the secondary receptors are immobilized nucleic acid probes that specifically recognize and hybridize with nucleic acids released following the application of the electric field. This embodiment therefore provides a hybrid two-stage solid phase binding assay, with a first stage involving the capture of cells onto an array of immobilization regions on a solid support via the primary receptors, and the second stage involving the capture of released nucleic acids by secondary receptors immobilized on the same solid support. Following the application of the electric field and the release of intracellular analyte, the reaction vessel is incubated for a period of time sufficient to enable the binding of released nucleic acids to the immobilized nucleic acid probes. The assay may then proceed according to methods known in the art, in which a sandwich assay is performed by adding labeled detector probes that are specific to the nucleic acids comprising the released intracellular analyte.

In another preferred embodiment, the secondary receptors are antibodies that specifically recognize intracellular analyte following the application of the electric field. As in the preceding embodiment involving the use of nucleic acid probes as secondary receptors, this embodiment also provides a hybrid two-stage solid phase binding assay, with a first stage involving the capture of cells onto an array of spots on a solid support via the adherent material (e.g. primary receptors), and the second stage involving the capture of released intracellular analyte by antibodies immobilized on the same solid support as the adherent material. Following the application of the electric field and the release of intracellular analyte, the reaction vessel is incubated for a period of time sufficient to enable the binding of released intracellular analyte to the immobilized antibodies. The assay may then proceed according to methods known in the art, in which a sandwich assay is performed by adding labeled antibodies that are specific to the intracellular analyte.

In a preferred embodiment, the signal from each spot in the preceding embodiments (involving the detection of intracellular analyte via immobilized secondary receptors) is an optical signal that may include, but is not limited to, signals produced by chromogenic, fluorometric, luminescent, chemiluminescent, electro-luminescent, or time-resolved fluorometric labels. The optical signal may be produced or facilitated by a single label, such as a fluorophore, or may be produced or facilitated by two or more labeled moieties, or may require the addition of further reagents such as signal-producing substrates.

Exemplary methods for preparing a solid support with adherent material and secondary receptors are henceforth described. Preferably, the adherent material comprises an antibody having an affinity for the cell surface, and the secondary receptors comprise nucleic acid probes (or synthetic analogs thereof) for binding intracellular analyte comprising nucleic acids (such as rRNA). The adherent material and the secondary receptors with appropriate functional groups can be immobilized on any surface known in the prior art following any known surface preparation methods to introduce appropriate reactive functional groups on the solid support. Examples of surface preparations can be deposition of small molecules such as organosilanes and thiol linkers by covalent interaction or macromolecules such as poly-L-Lysine and PEI by physical adsorption.

In an exemplary, yet non-limiting embodiment, a hetrobifunctional silane layer with functional groups, X—Si—X', can be deposited on any surface (Y) on which a silane layer can be applied to form Y—O—Si—X'. X' may be trimethoxy ($—OCH_3)_3$, triethoxy ($—OC_2H_5)_3$ or trichloro ($Cl_3$) and form Y—O—Si—X' chemistry upon hydrolysis. One example of such surface is hydroxylated surface of aluminum support, with a naturally or artificially processed oxide layer, and a hetrobifunctional silane layer is generated by Al—O—Si—X' formation. X may vary and covalently interacts with the respective functional group of capture ligand or cross-linker molecule to be attached to the silane layer via any appropriate chemistry. For example, X can be glycidyl functional group of glycidyloxipropyl-trimethoxysilane (GOPTS) or amino functional group of 3-aminopropyltriethoxysilane (APTS). Glycidyl functional group of GOPTS will interact readily with amino functional group of the molecule to be attached. However, an additional activation of amino functional group of APTS with any crosslinking chemistry, for example, 1-ethyl-3-(3-dimethylaminopropyl) carbodiimide) (EDC) and N-hydroxysuccinimide (NHS), will be required for covalent interaction with carboxyl functional group of the molecule to be attached. Optionally, amino functional group of APTS can be pre-activated with any known chemistry, for example, with glutaraldehyde homobifunctional crosslinker, to interact readily with amino functional group of the capture ligand to be immobilized. Alternatively, protein molecules with high affinity and specificity such as avidin or streptavidin can be immobilized on the functionalized aluminum surface via any suitable chemistry and a biotinylated capture ligand can be readily immobilized on the surface by biotin-avidin affinity interaction.

Once the surface preparation is completed, the adherent materials and the secondary receptors, which have been suspended in an appropriate buffer, can be dispensed on the desired region of the surface by liquid dispensing methods known in prior art. In the preferred embodiment, the adherent materials and the secondary receptors are suspended in a common buffer and therefore are dispensed together. In another embodiment, the secondary receptor is already bound on the adherent material by covalent or bio-affinity bonding. The resulting adherent material is suspended in an appropriate buffer for dispensing. These embodiments provide better consistency in manufacturing. In the third embodiment the adherent materials and the secondary receptors are suspended in separate buffers and are dispensed sequentially. After dispensing, using either approach, the surface is kept in an appropriate environment, which has been optimized in terms of temperature and ambient atmosphere, to allow for the formation of covalent bonding and evaporation of excess buffer. Then, the surface is washed to remove excess materials. Finally, the unbound reactive sites are blocked by methods known in the prior art.

Preferably, prior to lysis, a lysis buffer is flowed into the microfluidic channel to support efficient lysis of the adhered cells. After lysis, the released nucleic acids may be concentrated to the surface and retained at the surface by the application of voltage to the electrodes 17 and 18. Preferably, the voltage is applied in a uni-polar AC form, under pulsed operation, as described above in the concentrating section, for concentrating the cells at the anode side of the cell. The lysis buffer may then be removed, and a hybridization buffer can be flowed into the chamber while retaining the released nucleic acids in close proximity to the immobilized probes (e.g. by maintaining the pulsed voltage). After providing the hybridization buffer and releasing the applied electric field, hybridization occurs. Preferably, the hybridization buffer further comprises labeled detector probes. Alternatively, an additional step may be provided in which the hybridization buffer is removed and a detector probe solution is flowed into the chamber to facilitate detection of the bound intracellular nucleic acids.

For example, a detector probe may constitute an oligonucleotide labeled with a chemiluminescent enzyme such as horseradish peroxidase. In this exemplary embodiment, the unbound labeled oligonucleotide is removed in an additional wash step, and the assay signal is optically detected following the detection of a chemiluminescent substrate.

A wide range of alternative assays may be employed for the detection of the bound nucleic acids, such as use of PNA labeled probes and molecular beacon assays. During target hybridization, high cationic concentration in the buffer neutralizes the negative charge on the single stranded DNA probe and accelerates hybridization kinetics. Therefore, in the assay steps previously described, a low-ionic lysis buffer is replaced with a high-ionic hybridization buffer. The neutral charged backbone of PNA allows a low ionic strength buffer for target hybridization, which is advantageous for lysis immediately followed by hybridization in the same low ionic buffer. In another approach using a molecular beacon assay, the fluorescent signal of molecular beacon is detected only upon target hybridization and therefore separation of hybridized probes and unbound probes is not necessary, eliminating a wash step following hybridization. Molecular beacons can be designed as either DNA or PNA backbone as know in the art, allowing the flexibility of ionic concentration selection for the lysis buffer. Instead of using as detector probes, molecular beacon probes can be immobilized to the solid support as the secondary receptors to capture released intracellular nucleic acids following lysis, thereby providing a hybrid two-stage solid phase binding assay without requirements of an additional detector reagent and wash steps.

In another preferred embodiment, each spot in the array on the solid support further comprises an electrode, with each electrode electrically connected to an externally addressable contact pad. Preferably, a reference electrode is additionally provided in fluidic contact with the array electrodes. Accordingly, an electrochemical label and substrate may be employed for use in such an embodiment for the spatially resolved measurement of an electrically assay signal.

Devices according to various embodiments as disclosed herein may be in the format of a kit enabling users to customize and/or select the adherent material and/or secondary receptors appropriate to target cells and intracellular analytes of interest. The kit preferably comprises the elements required for at least one of concentration, lysis and detection as described above and furthermore provide a means for the user to provide user-selected adherent material (for example, primary antibodies targeting a cell surface) and/or secondary receptors (e.g. antibodies or probes for binding intracellular analyte of interest) to the solid support.

In a preferred embodiment kit comprises a substrate containing an open microfluidic channel, exposing the solid support, a separate top plate, and optionally a sealing adhesive or clamping structure for contacting the top plate with the substrate and enclosing the microfluidic channel for use with a liquid sample. The user may apply capture ligands to the prepared solid support by manual or automated dispensing (e.g. spotting) methods.

When the capture ligands have been applied and all excess material removed the top plate will be applied to the channel and fixed there by means of, for example, pressure sensitive adhesive pre-applied to either the top or bottom plate. The device, so prepared, may then be employed to carry out the aforementioned method steps according to various embodiments (e.g. concentration, lysis and detection) as described elsewhere in this disclosure.

The open channel may comprise a surface prepared to bind capture ligands of interest over the entirety of the surface providing the user with the flexibility to select any appropriate spatial configuration for the array. Tools and instruments are available commercially to aid in the application of arrays to solid supports. A preferred embodiment provides a pre-placed mask on the solid support which isolates discrete binding regions forming the array. The mask allows droplets of distinct capture ligands to be placed on each binding region while preventing these droplets from spreading to neighboring regions.

As an example, the mask may comprise a thin plastic film with holes defining potential immobilization regions, where the plastic film is preferably fixed to the solid support by an adhesive such as a removable adhesive backing. The droplets of desired capture ligands would be applied to the binding regions by, for example, a pin applicator or a pipette. Following completion of the application of capture ligands (which may comprise either or both of the cell surface adherent material and secondary receptors for binding intracellular analyte) and removal of excess material, the mask may optionally be removed from the solid support and the microfluidic channel may be sealed by providing the top plate as noted above. A more elaborate mask could be envisaged which would provide for enhanced control of droplets during application of the capture ligands for ease of use by the user.

The solid support of the foretold open platform kit can be prepared by procedures presented in the following two non-limiting examples. In the first example, the polished aluminum support plates are cleaned with water then rinsed twice with methanol and air-dried. 2% 3-Aminopropyl Triethoxysilane is prepared in 95% Methanol 5% water and the plates are immersed in silane for 5 min. Then, the plates are rinsed in methanol twice, air-dried and baked at 110° C. for 10 min. After cooling, the plates are immersed in 2.5% glutaraldehyde homobifunctional crosslinker in phosphate buffered saline, pH 7.4 at room temperature for 1 hour. The plates are rinsed thoroughly with water and air-dried. The reaction zone of the microfluidic channel is defined by applying a double-sided adhesive spacer on the treated surface of the plates. The user will immobilize antibody or amino-labeled oligonucleotide capture probe, or a mixture thereof as illustrated in Example 2 below, in a basic pH binding buffer such as carbonate buffer pH 9, by manual or automated spotting method, wash unbound materials and block non-specific binding sites by method of choice before applying the top plate.

In the second example, 2.5% glutaraldehyde homobifunctional crosslinker in phosphate buffered saline, pH 7.4 will be applied only at the pre-defined areas of the reaction zone with isolated binding areas created by removable mask with adhesive backing. The user will apply a droplet of antibody or amino-labeled oligonucleotide capture probe, or a mixture thereof, in a basic pH binding buffer such as carbonate buffer pH 9, over the pre-defined areas, allow immobilization of the capture ligands, wash unbound materials, remove the removable mask and block non-specific binding sites on the entire reaction zone by method of choice before applying the top plate.

Devices according to various embodiments as disclosed herein may be employed for the screening of biological samples for the detection of the presence of microorganisms above a certain threshold detection limit. This may be accomplished by flowing a sufficiently high quantity of sample through the device to obtain a measurable signal, while employing the above mentioned techniques for cell retention and concentration. Assuming a retention efficiency of less than 100%, the volume of the sample may be adjusted to ensure a minimum sensitivity requirement is established. In other words, the amount of sample that is flowed through the device is adjusted to compensate for the sensitivity requirements of the particular clinical application. As will be apparent to those skilled in the art, this may be achieved in a calibration step. In a non-limiting example, if the clinical sample is blood and a detection limit of 100 CFU/ml is required, then the total sample volume that is used for concentration and detection must be 100 times that of the case where the sample is urine and a detection limit of $10^4$ CFUu/ml is desired. In one embodiment, the device can be operated in a "flow-through" regime, where a volume of sample is employed that is substantially larger than the volume of the device, so as to improve the limit of detection to address clinical performance requirements.

As illustrated in the preceding example, the amount of sample required to achieve a certain detection limit is variable across different clinical sample and specimen types. Selected embodiments support the continuous flowing of sample through the device until the appropriate cell concentration has been achieved by monitoring, for example, an optical signal such as auto fluorescence or light scattering, in the concentration zone.

In a particular embodiment in which the adherent material comprises primary receptors, the primary and/or secondary receptors may be chemically attached to a hydrogel, such as a polyacrylamide based hydrogel (e.g., Yu et al., BioTechniques 34:1008-1022, 2003). Acrylamide monomers may be copolymerized with different probes (e.g., oligonucleotides, DNA, proteins, aptamers, etc.) by photoinduced polymerization of methacrylic modified monomers. The hydrogels may be attached to glass, silicone or other surfaces. Avidin-modified receptors may be attached to hydrogels containing biotin-modified monomers. The use of hydrogels improves the stability of receptors, such as proteins, and can maintain their binding activity for six months or longer (Yu et al., 2003). Hydrogel based microfluidic devices may be utilized in combination with optical detection methods discussed above.

The primary and/or secondary receptors may be attached to the surface of the network-like hydrogel or alternatively may be embedded within the hydrogel to increase their stability. In addition hydrophilic nature of hydrogel prevents non-specific binding to the solid support, resulting in a lower background signal. The three-dimensional structure of hydrogel provides larger surface area for immobilization of receptors and as a result, assay signal intensity is improved. Where the receptors are embedded within the hydrogel, the aforementioned binding assays for the presence or absence of intracellular analyte may also be performed within the gel. The hydrogel may be used to confine the reaction and/or reagents in localized manner to improve the sensitivity of the assays. As noted above, such assays may be performed using, for example, nucleic acid detection or immunoassays. In a preferred embodiment, the primary and/or secondary receptors may be attached to the surface of the brush-like hydrogel in which hydrogel polymers are extending like a brush from the surface, providing higher surface area for receptor immobilization than the aforementioned network-like hydrogel. In addition, the receptors are entirely exposed to the aqueous medium and therefore specific binding reactions between the receptors and analytes are further enhanced. The use of the brush-like hydrogel for arrays has been disclosed in U.S. Pat. No. 6,994,964, which is incorporated herein by reference in its entirety.

The preceding embodiments involving the use of secondary receptors may be adapted for the specific detection of cells in a number of ways. In a preferred embodiment, the adherent material comprises primary receptors, and both the primary and secondary receptors immobilized at a given spot in the array are specific to a given cell or cell type (or cell genus, species, or strain). In another embodiment, the adherent material provided at each spot in the array bind with a wide range of cell types, and the secondary receptors at each spot are specific to intracellular analyte from a given cell or cell type. In another preferred embodiment, the adherent material comprises primary receptors that are specific to a given cell or cell type at each spot, and the secondary receptors bind with intracellular analyte from a wide range of cell types. In embodiments in which the secondary probes provided at each spot are specific to intracellular analyte from a given cell or cell type, and where different spots target different cells or cell types, the labeled detector reagents are preferably specific to the intracellular analyte, and thus provide an additional degree of specificity. Such labeled detector reagents may be provided as a multiplexed set of labeled reagents in a liquid form that is added to the reaction.

In contrast to the above embodiments involving solid-phase detection of the intracellular analyte, alternative embodiments utilize a homogenous assay for the detection of intracellular analyte. The homogenous assay involves the addition of one or more reagents that react with released intracellular analyte to produce a detectable signal. Embodiments as disclosed below advantageously enable the use of a homogenous assay for the local detection of intracellular analyte after lysis or electroporation, in close vicinity to the spot onto which a cell is bound.

The additional reagents required for the homogeneous assay may be provided to the reaction vessel or chamber, (i.e. contacted with the solid support) prior to the application of the electric field and the release of the intracellular analyte. Accordingly, upon release of the intracellular analyte, the homogenous reaction is initiated immediately due to the presence of the additional reagents. This in turn enables the detection of an assay signal that, while originating from a homogeneous reaction, is generated locally in a spatial volume that is in close proximity to the spot onto which the cell was initially immobilized.

The reagents are preferably selected to produce an assay signal over a time interval that is less than the time interval over which intracellular analyte may diffuse to an adjacent spot, thereby enabling spatially-resolved detection of the assay signal. In other words, by selecting homogeneous assay reagents that rapidly produce a signal relative to the timescale of lateral diffusion, the assay signals from each individual spot may be spatially resolved and detected in a multiplexed format.

Since the very nature of the homogeneous reaction requires that the same homogeneous assay reagents are present at each spot, it is preferable that the homogeneous assay reagents detect an intracellular analyte that may be common to cells bound at all spots in the array. Accordingly, the specificity for a particular cell bound at a particular spot is provided by the primary receptors that bind the cell to the solid support prior to the application of the electric field.

In a preferred embodiment, the homogenous assay is an assay for endogenous intracellular adenosine triphosphate (ATP), and the homogeneous reagents are preferably luciferin and luciferase. The reaction of endogenous ATP (released by bound cells following the application of an electric field) with luciferin and luciferase produces luminescence that will initially be produced from a volume that is spatially localized near the array spot upon which the cell was initially bound. In a preferred embodiment of the invention, an optical imaging device such as a charge-coupled device (CCD) camera is employed to image the luminescence from the homogeneous reaction prior to the loss of spatial resolution resulting from lateral diffusion.

When a homogeneous assay is utilized for the detection of intracellular analyte, the sample may be pre-treated with a substance that inactivates extraneous intracellular analyte that may be originate in the sample from additional source such as cell types that are not intended to be assayed (for example, red blood cells in an assay for bacteria in a blood sample). In a preferred embodiment in which the homogeneous assay is provided to detect endogenous ATP, a sample pre-treatment step may include providing ATPase to the sample to inactivate any free ATP in the sample.

The preceding embodiments may also be combined with an additional binding assay that is performed prior to the release of intracellular analyte (i.e. prior to the application of the electric field) for the detection of identification of cells bound to the array. In this embodiment, additional labeled binding moieties comprising labeled receptors or ligands are included that specifically bind with cell surface analyte or receptors on the cell surface. During a subsequent wash step, unbound or non-specifically bound labeled binding moieties are removed. As will be apparent to those skilled in the art, the labeled binding moieties preferably comprise a multiplexed set of labeled binding moieties, with each member in the set specifically binding to a cell or cell type targeted by the array.

The labeled binding moieties preferably produce optical signals that enables the detection and/or quantification of cells bound to the array by imaging or microscopy. As discussed above, the labeled binding moieties may include, but are not limited to, signals produced by chromogenic, fluorometric, luminescent, chemiluminescent, electro-luminescent, or time-resolved fluorometric labels. As will be appreciate by those skilled in the art, the optical signal may be produced or facilitated by a single label, such as a fluorophore, or may be produced or facilitated by two or more labeled moieties, or may require the addition of further reagents such as signal-producing substrates. The optical signal is preferably imaged by an imaging device such as a CCD camera, and the spatially-resolved multiplexed signal may be utilized to detect and/or quantify the binding of cells to the array spots prior to the application of the electric field. In a preferred embodiment, sufficient optical resolution is utilized to detect the cell morphology.

In yet another preferred embodiment, cells bound to the primary receptors are detector and/or quantified by the aforementioned method utilizing labeled binding moieties, and the viability of the bound cells is determined following the release of intracellular analyte according to the aforementioned embodiment of the invention.

In an exemplary embodiment, the array is configured to specifically bind multiple types of cells, in which cells of unique genus, species, or strain are bound to each spot in the array. Initially, bound cells are identified by the aforementioned binding assay. Homogeneous assay reagents comprising luciferin and luciferase are subsequently contacted with the array, and an electric field is applied to locally release ATP from the bound cells. The viability of the cells (e.g. a determination of whether the cells are alive or dead) is determined by correlating the signal obtained from the homogeneous ATP assay with the presence or amount of cells determined from the initial binding assay. This embodiment may be further adapted for use in multiplexed arrays for the determination of antibiotic resistance, whereby the viability of microorganisms exposed to antibiotics can be determined and an indication of the susceptibility or resistance of the microorganisms to the antibiotics can be obtained.

Methods of Detection

Selected non-limiting examples are henceforth provided describing methods for the detection of microorganisms in a sample such as blood, urine or a growth medium into which a biological sample suspected of containing microorganisms may have been inoculated and incubated. In a first ATP-based detection method, the following steps are preferably followed:

1) Sample filtering: The sample is optionally passed through a filter unit to remove eukaryotic cells, ATP, and particulate matter. The filtered sample may be continuously pumped via an inlet port through a reaction chamber.
2) Concentrated layer formation: By applying an electric field, the microorganism cells may be optionally (if high sensitivity is desired) brought into a layer at the vicinity of the lower chamber wall.
3) Solid phase cell retention: Microorganism cells are captured and retained onto an array of specific capture ligands.
4) Wash: The debris nonspecifically retained is preferably removed with a wash step.
5) Detection reagent: The reaction chamber is filled with a solution containing Luciferin and Luciferase.
6) Cell lysis: The cells are lysed by briefly applying a large electrical field to the array.
7) Signal detection: The biosites are imaged and the bioluminescence signal is measured.

These steps can be understood by referring to FIGS. 6-9 which schematically describes the basic assay steps utilizing the ATP-based detection methods. It should be understood that in applications where high sensitivity is not required some of the steps may be omitted and thereby the assay method is simplified. For instance, when the microorganism concentration in a sample, such as positive post-culture growth media, is very high, the concentration step may be ignored. However, in the following section, the process will be described with all steps included.

Figure 6:
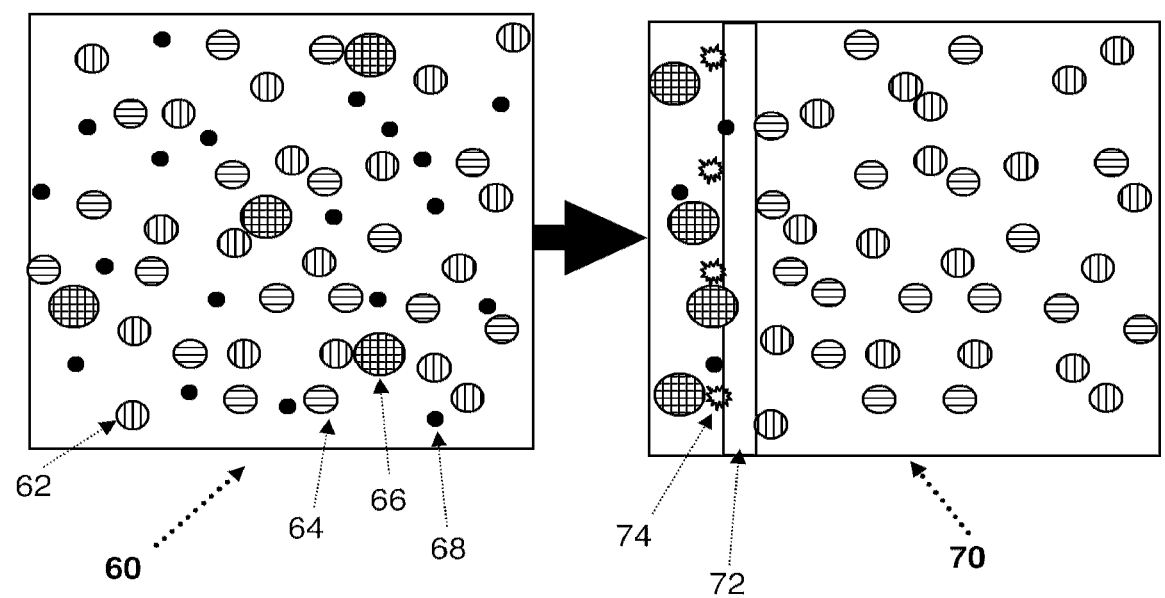
FIG. 6 shows a schematic of the sample before and after filtering.

A typical sample, represented in FIG. 6 at 60, contains microorganism cells, such as 62 and 64, eukaryotic cells 66 and the background ATP molecules 68. The eukaryotic cells have far more ATP than microorganism cells, so even a small amount of these cells, if not successfully removed from the reaction chamber during the washing step, may release large amounts of ATP resulting in unreliable assay results. Devices for removing these cells are known in the prior art (U.S. Pat.

No. 7,419,798) and they work by filtering out the eukaryotic cells with a filter that allows microorganism cells to pass through. Typically this is accomplished by having pores in the filter of a particular nominal size. For instance, filters of particular of relevance have pores sufficiently large to allow passage of microorganism but small enough to prevent passage of eukaryotic cells present in the fluid sample of interest. Microorganisms are typically smaller than 1 micron in diameter; platelets are approximately 3 microns in diameter; and nucleated eukaryotic cells are typically 10-200 microns in diameter.

Preferably, a filtering unit 70 is employed, which comprises a filter 72. The sample may contain ATPase enzymes, and the fitler may include immobilized ATPase enzymes 74 which remove the background ATP of the sample for further reducing the assay background and enhancing the assay sensitivity.

Figure 7:
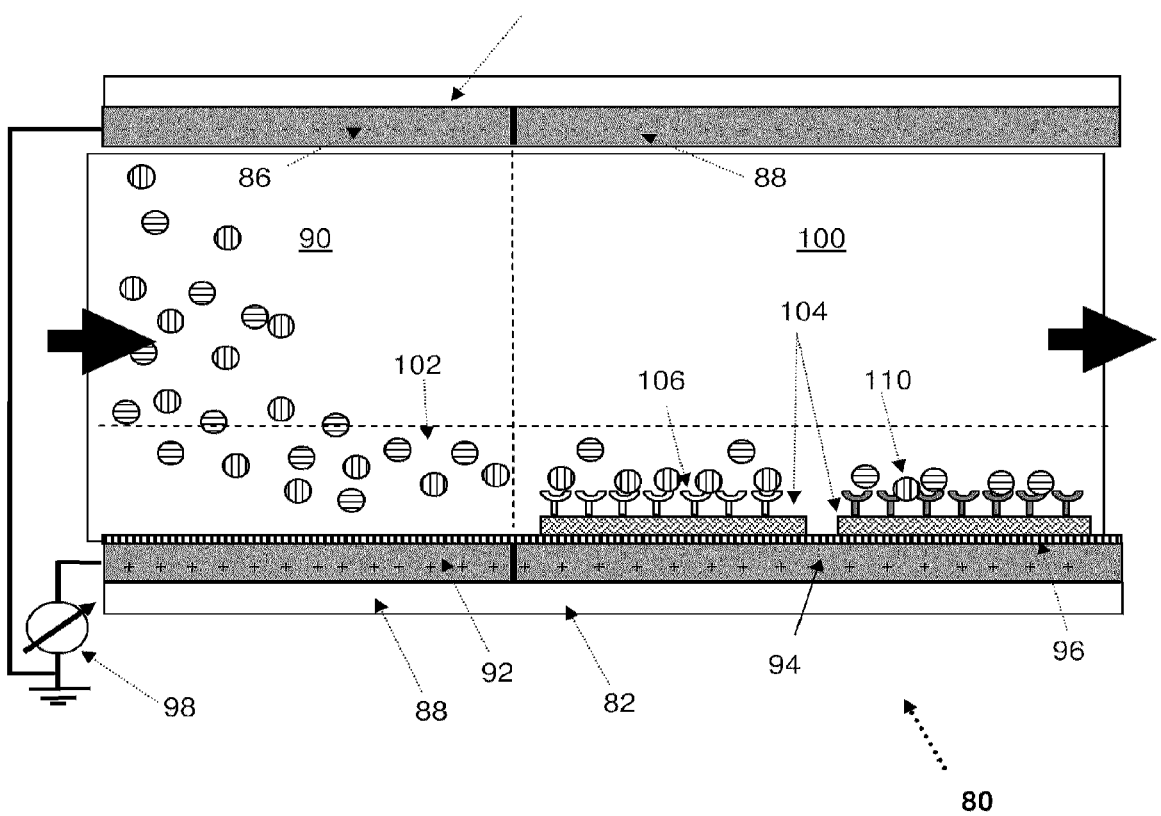
FIG. 7 shows concentrated layer formation and cell retention at immobilization regions.

FIG. 7 schematically shows a portion of a concentration, lysis and detection device 80 similar to that shown in FIGS. 1, 2 and 5, comprising a concentration area 90 and a reaction area 100. The device includes lower and upper flat plates, 82 and 84, separated by means of a spacing element (not shown), which forms and seals the chamber. As described above, this type of chamber can be manufactured according to known methods, such as those disclosed in U.S. Pat. Nos. 5,240,618 and 6,180,906. Typically, the spacer between the plates 82 and 84 is made from MYLAR® or similar material which is slightly deformable under an applied clamping pressure. The spacer thus serves to define the side walls of the chamber, provides the fluid seal, and electrically insulates the plates from each other. The dimensions of length, L, width, W, and height, H, of the reaction area 100 in the chamber are in the order of 2 cm, 2 mm and 100 µm, respectively.

The fluid is introduced into the chamber through the inlet port and is conducted into the waste chamber via outlet port (these ports are shown in FIG. 1). The chamber elements are illustrated in greater detail in the cross sectional views of FIGS. 2 and 3. The upper plate 84 preferably is made from a transparent material. A thin and semitransparent layer of metal or other conductor material 86 is been coated over the inner surface of the upper plate (thickness exaggerated in the Figure). Therefore the conductor is in physical contact with the fluids. The conductor material is shown as two distinct sections 86 and 88 in FIGS. 7 and 8, but in a second embodiment there is no physical separation between the sections and they form a single conductive surface. The bottom plate 82 can be made of a metal plate or a conductor coated on a dielectric substrate 88 in which the conductor consists of two distinct sections 92 and 94 located opposite corresponding conductor sections on the upper plate as illustrated in FIG. 7. In this case the bottom plate conductor is also in physical contact with the fluid in the chamber and is defined as the Top Conductor-Bottom Conductor (TC-BC) configuration. In another embodiment, designated as Top Conductor-Bottom Dielectric (TC-BD) configuration, the bottom plate sections 92 and 94 are made of conductor or semiconductor material (such as Al or Si) with the inner side of the plate oxidized to form, or coated with, a thin layer of dielectric 96. Under some circumstances it may also be desirable for the above configurations to consist of single continuous conductive sections on the upper and bottom surface respectively spanning the electrically active length of the chamber.

The voltage necessary at different stages of the assay are applied by the voltage source 98. The source is connected to the electrically conductive surfaces of the plates by electrical leads. As it will be discussed in the following, electrical cell lysis requires brief fields of order 5 kV/cm. Therefore, the voltage source 98 should be able to be switched from 0 to about 100 Volts in millisecond timescales.

The concentration step may be necessary in applications requiring high assay sensitivity of less than 10,000 CFU/mL. This step is included to remedy a key limitation on the assay sensitivity imposed by the dependency on the passive diffusion of microorganism to the capture ligands. The diffusion rates of some microorganisms are extremely small such that they diffuse only about 1 µm in one second. The concentration step of the present embdodiment can be understood by referring to FIG. 7. When fluid flows into the reaction chamber, a parabolic velocity profile (Poiseuille flow) is established across the thickness of the chamber due to the no-slip boundary condition at the chamber walls. Application of a voltage difference to the plates 86 and 92 establishes a transverse electric field, which induces a transverse displacement of microorganism cells across the chamber toward plate 92. As the cells approach the wall, their overall motion is eventually halted. The final equilibrium position or steady state distribution across the thin dimension of the chamber is determined by the balance of the primary driving force and the opposing forces, which are produced by displacement or hydrodynamic effects. The region 102, where the majority of the microorganism resides, is termed as the concentration layer.

If the dielectric layer 96 is not included, then DC operation is preferably employed, and a sustainable field may be achieved with the addition of a red-ox couple to the sample. A well known red-ox couple is quinone/hydroquinone. Preferably, dielectric layer 98 is provided on the conductive layers 92 and 94, and concentration is achieved by rapidly switching the voltage on a millisecond timescale to achieve net drift of the cells relative to the background ions, as described in the sections above.

Microorganism cells transported to the vicinity of the array of immobilized receptors 104 within the reaction area 100 may collide with a specific capture ligand 106 and be specifically retained. The array spots may have arbitrary geometries, but in a preferred embodiment they are rectangular in shape with dimensions of around 0.5 mm×2 mm, with the longer dimension aligned perpendicular to the chamber's axial flow direction. The capture ligands are preferably antibodies that recognize cell surface antigens.

As will be known to those skilled in the art, the method by which the antibodies are immobilized to form the array depends on the material surface properties. In a preferred embodiment, plate 82 is Al with a thin layer of $Al_2O_3$ forming dielectric layer 96. The surface of aluminum oxide may be modified to create hydroxyl groups followed by coating with a heterobifunctional silane layer, creating functional groups to interact covalently with the capture ligands. The non-specific binding of microorganism and other undesired materials to the surface is prevented by treating the surface with a suitable blocking buffer.

To further improve the assay sensitivity, the surface of plate 82 may be coated with a three-dimensional brush-like polymeric functionalized hydrogel layer. The capture ligands are immobilized on the hydrogel layer by covalent interaction with functional groups on the polymer brushes. The hydrophilic polymer inhibits non-specific microorganism binding to the surface thereby reduces the background signal. Polymer brushes provide a much larger area of substrate for capture ligand immobilization, resulting in multiplicity of binding sites for the target microorganism cells and enhancement of the signal detection. In this method, the requirement for treatment of the surface with a blocking buffer is eliminated because of the inherent inhibition of non-specific binding on the hydrogel layer.

The specificity of the receptors (e.g. antibodies) employed to form the array of spots may be tailored depending on the application. For example, it may be desirable to have specific capture ligands for different strains of *E. coli* that will not cross-react with each other. In another non-limiting example, it may be desirable to have a capture ligand that binds to many or all *E. coli* strains, and another that binds to many or all species or strains of the *Streptococcus* genus.

Figure 8:
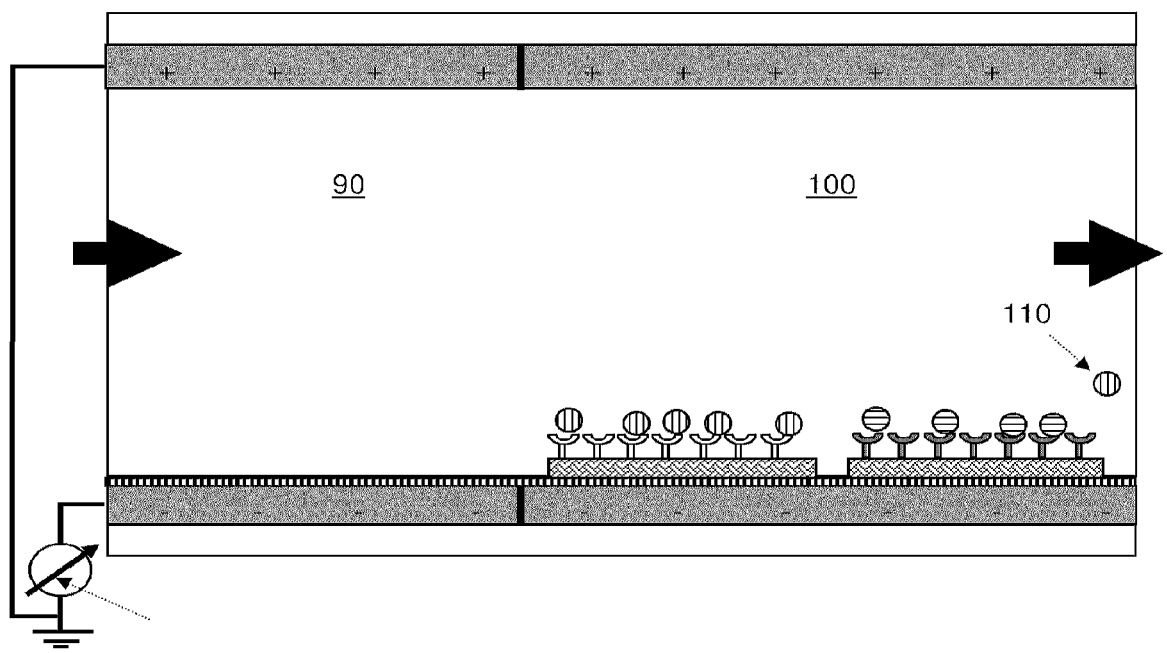
FIG. 8 shows a schematic of a wash process.

The washing process, which is depicted in FIG. 8, is performed to remove non-specifically bound microorganism cells. These include cells 110 that had retained outside of their corresponding (specific) array spot. Flushing the reaction chamber with a washing buffer may not be very effective as the fluid velocity at the proximity of the array is close to zero under laminar flow conditions. For more effective washing, electrophoretic forces may be used to provide discrimination force between specifically and nonspecifically bound cells. For this purpose, a slightly reverse biased voltage is applied to the electrodes within the reaction area 100 before and/or during washing.

Figure 9:
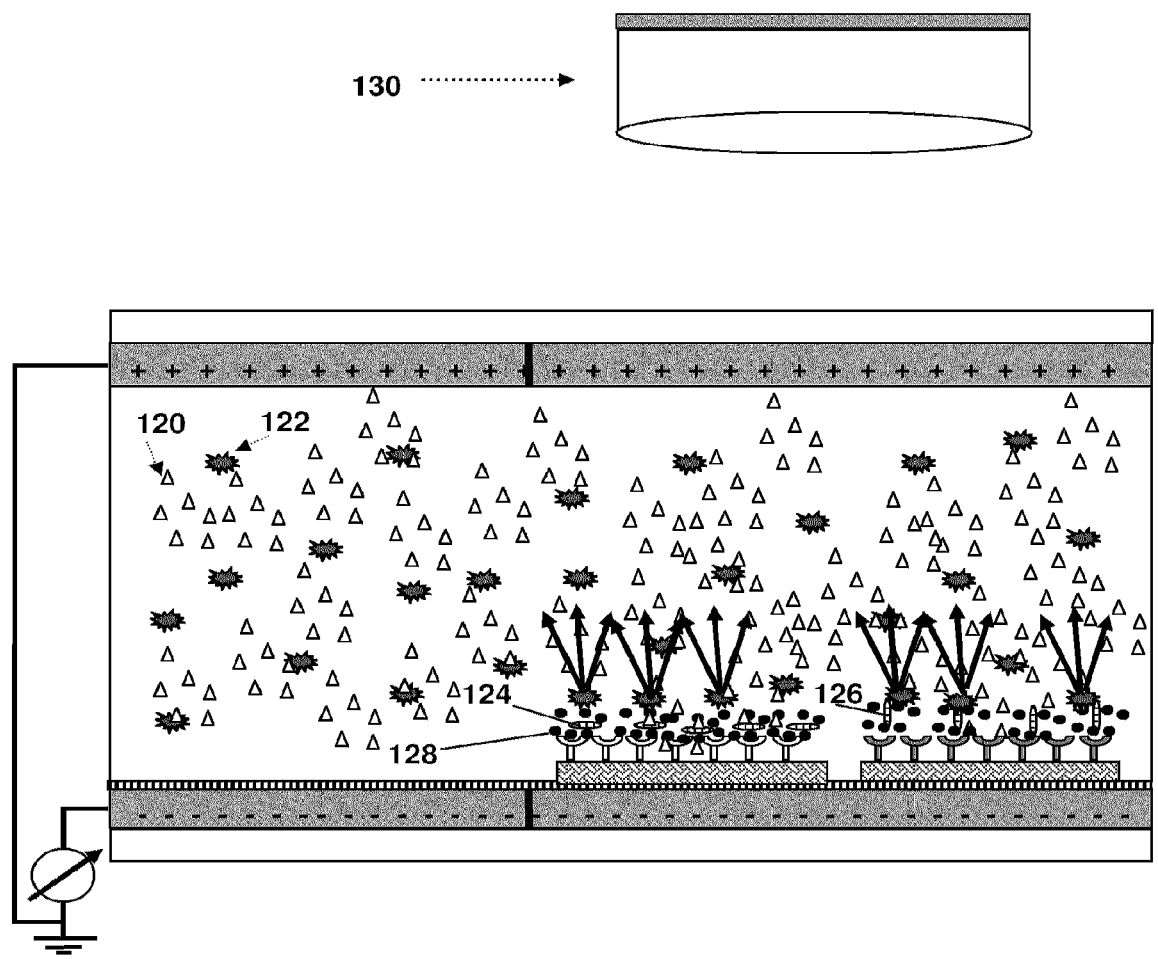
FIG. 9 shows a cell lysis and ATP-based signal detection step.

FIG. 9 schematically presents the last two steps when the ATP-based detection scheme is employed. Prior to the cell lysis the chamber is filled with a solution containing Luciferin 120 and Luciferase 122. Then, a high voltage pulse with a short duration in the sub millisecond level is applied on the electrodes 88 and 94. This places the bound cells in a high field in the order of few kV/cm, which opens pores in the cell membrane and allows the cellular content, amongst which there are nucleotides such as ATP, to be released. In FIG. 9 the lysed cells are indicted by 124 and 126 and the released ATP by 128.

Theoretically, it is possible to measure a wide range of the nucleotides that are released by the cell lysis with sensitivity provided by use of one or more of the many enzyme based assay systems that are available in the art. However, in this preferred method, ATP is readily measurable by assay with a variety of enzyme/enzyme substrate combinations. For the rapid and efficient determination of levels of released ATP it is especially preferred to utilize enzyme reactions which result in production of luminescence, most conveniently using luciferase (U.S. Pat. No. 4,200,493). The released ATP is quantifiable with commercially available reagents using bioluminescence wherein it is used to drive oxidation of luciferin under catalysis by luciferase resulting in the emission of light. The quantum efficiency of this reaction is extremely high and the presence and amount of light detected by optical system 130 (FIG. 9) gives a measure of ATP released and thus of the presence and numbers of the target organisms.

One of the main advantages of the present method is that due to rapid electrical cell lysis and immediate onset of the enzymatic reaction the signal detection, and subsequent cell identification and quantification, is accomplished before the released ATP can diffuse to the adjacent array spots. This enables multiplexed assaying of many cells in a single reaction chamber. The characteristic distance, l, which a particle with diffusion coefficient D will diffuse in time, t, is $$l=\sqrt{Dt}$$

The diffusion coefficient of small molecules such as ATP is in the range of $5\times10^{-6}$ cm$^2$/s. Therefore, the characteristic time to diffuse 500 μm, which is the typical separation of the immobilization regions, is estimated to be 500 s. Thus simultaneous detection of multiple cells is possible in such an array of immobilization regions is possible since the characteristic time is much longer than the combined lysing and detection times.

As it is known in the art, designing nucleic acid probes is generally easier than preparing highly specific antibodies. Accordingly, and as described above, in a second example, antibodies are used to capture the microorganisms and the intracellular nucleic acid material of the cells can be used as the target for identification through hybridization with specific nucleic acid probes. The specificity of the antibodies can be relaxed in accordance with the range of target microorganisms which are sought. In this second detection method involving the detection of intracellular nucleic acids, the following steps are preferably followed:

1) Sample filtering: The sample optionally is flowed through a filter unit to remove eukaryotic cells or other particulate matter.
2) The filtered sample is continuously pumped via an inlet port through a reaction chamber.
3) Wash: The debris nonspecifically retained is preferably removed with a wash step.
4) Concentrated layer formation: By applying an electric field, the microorganism cells may be optionally (if high sensitivity is desired) brought into a layer at the vicinity of the lower chamber wall.
5) Solid phase cell retention: Microorganism cells are captured and retained onto an adherent material (preferably an array of specific capture ligands)
6) The reaction chamber is filled with a solution containing labeled nucleic acid detector probes.
7) Cell lysis: The cells are lysed by briefly applying a large electrical field to the immobilization regions.
8) Incubation: The released rRNA is allowed to be hybridized with both immobilized nucleic acid capture probes and the labeled nucleic acid detector probes.
9) Wash: The excess unbound labeled nucleic acid detector probes are removed
10) Signal generation and detection: Signals from the labeled probes are measured (preferably the array is imaged and an optical signal is measured).

An important aspect of this detection example is that it enables rapid and sensitive identification of microorganisms for which a specific antibody is not available or not practical for any reason. In this case nucleic acid content of the microorganism, preferably rRNA, can be detected as an identifier since designing specific probes for rRNA is relatively achievable. The nucleic acid hybridization-based method is intended for this application. In this case a less specific antibody, or even a non-specific yet cell adherent surface may be used in the immobilization regions to capture all of the target species and strains.

An example is the case when the goal is detecting a given strain of a microorganism and specific antibody is only available with adequate specificity up to the species level. A remedy offered by the present method is the following. A specific nucleic acid capture probe for the strain specific rRNA is prepared and immobilized alongside with the available antibody at, within, or adjacent to the same array spot. Then, the assay proceeds via the sequences represented by FIGS. 7-8 and 10-11.

After the microorganism cells are captured by the onto the array and optionally washed, the reaction chamber is filled with a buffer that is selected to support the lysis of the adhered cells, and optionally to further support the hybridization of released nucleic acids to bound probes in the array with an appropriate stringency. The buffer may further comprise labeled detector probes for subsequent detection of hybridized nucleic acids bound to the array. Suitable labels include, but are not limited to, enzyme indicators.

Preferably, as described above, the buffer is selected to provide efficient lysis of the adhered cells, and the released nucleic acids are subsequently drawn to the surface and retained at the surface by the application of voltage to the electrodes 88 and 94. Preferably, the voltage is applied as described above for concentrating a charged species at the anode side of the cell, e.g. under pulsed operation. This allows the lysis buffer to be removed and replaced with a hybridization buffer while retaining the released nucleic acids in close proximity to the immobilized probes. After providing the hybridization buffer, the field may be released, allowing hybridization to occur. Preferably, the hybridization buffer further comprises labeled detector probes. Alternatively, an additional step may be provided in which the hybridization buffer is removed and a detector probe solution is flowed into the chamber to facilitate detection of the bound intracellular nucleic acids.

A high voltage pulse with a short duration in the sub millisecond level is applied on the electrodes. This places the bound cells in a high field in the order of few kV/cm to open cell membrane and allow the cellular content, including nucleic acids such as rRNA, to be released.

Figure 10:
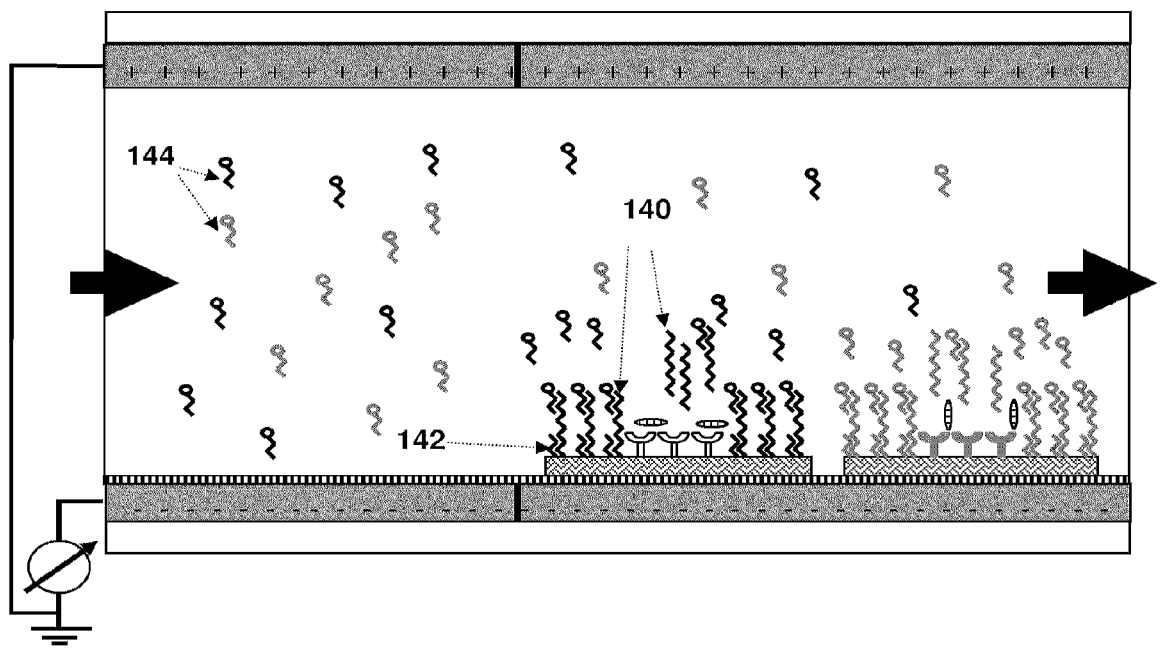
FIG. 10 shows cell lysis and nucleic acid hybridization.

FIG. 10 illustrates the binding of release rRNA 140 to immobilized probes 142 residing within the array spots. Also shown are detector probes 144 in solution, which bind to the released rRNA to facilitate detection in the form of a molecular sandwich assay.

The diffusion coefficient of the rRNA molecules is in the range of $10^{-8}$ cm$^2$/s (Biosensors and Bioelectronics 20 (2005) 2488-2503). Therefore, the characteristic diffusion distance in 1 s is about 10 µm. This indicates that for an appreciable period following the cell lysis, the concentration of the released of rRNA, 140, in the vicinity of the immobilized nucleic capture probes 142, will be very high. This high target concentration minimizes the time needed for target-capture probe hybridization. Thus an appreciable fraction of the released rRNA may be hybridized to the nucleic acid probes 142. These bound rRNA will also be hybridized to the labeled detector nucleic acid detector probes, comprising a sandwich assay as described above. The unbound or nonspecifically bound detector probes are removed by a washing step, also described above in the recited method steps of the example.

Figure 11:
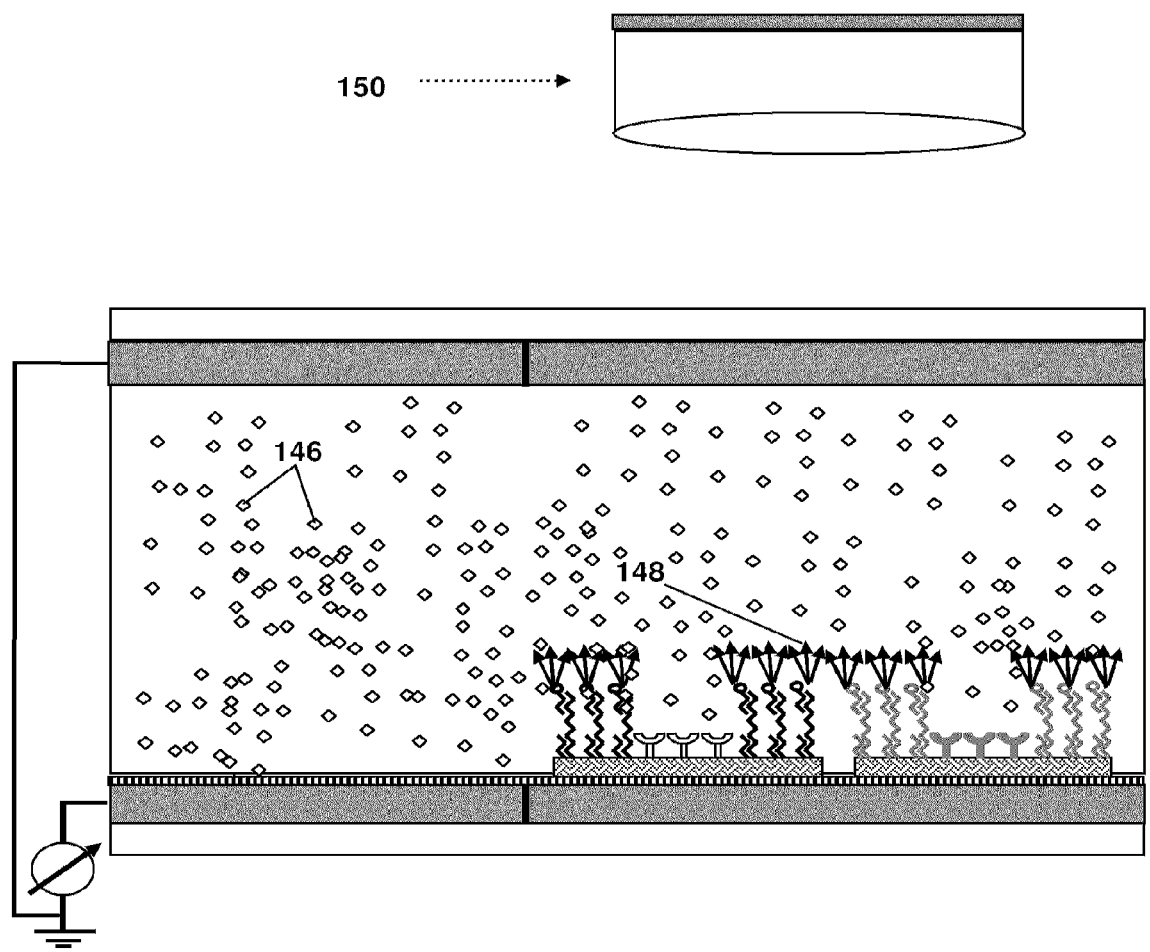
FIG. 11 shows nucleic acid hybridization-based signal detection.
Figure 12:
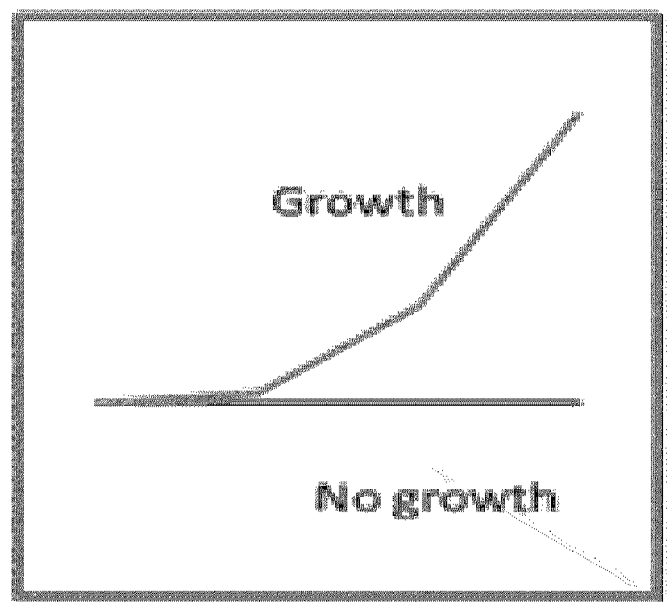
FIG. 12 illustrates a method of determining the antibiotic susceptibility of a bacterial sample according to an embodiment of the invention.

The detail of detecting the bound labeled nucleic acid detector probes is determined by the type of the label. A non-limiting embodiment is shown in FIG. 11, where the label is an enzyme-catalyzed reaction that generates chemiluminescent signal. The reaction is initiated by filling the reaction chamber with an appropriate substrate 146. The signal 148 is recorded by the optical system 150.

Additional Applications of Electroporation

One application of reversible electroporation is to release the smaller molecules, such as ATP, while maintaining the viability of the cell for the purpose of cell activity monitoring. In this case, a transmembrane potential of the order of 0.2-1.0 V is generated by applying a strong voltage difference to the electrodes. The resulting electric field generates pores in the cell membrane. These hydrophilic pores enable large and charged molecules, which are normally incapable of crossing the membrane, to leak out by diffusion.

The application of the reversible electroporation is not limited to the release of cellular contents, and other applications are considered within the scope of embodiments of the present invention. Electroporation can be applied for any cell type including plant cells and cultured cells for the delivery of molecules such as DNA, RNA, proteins, drugs and dyes into the cells. One exemplary embodiment involves the detection of only live cells, specifically retained by captured ligands, using a dye which is impermeant to live cells and which can access the interior of the cells only upon transient electroporation. Another approach for detecting intracellular targets, is the introduction of fluorescent molecular beacon probes for live cell RNA detection as described by Bao et al. (Annu Rev Biomed Eng. 2009; 11: 25-47).

Other applications of reversible electroporation include gene delivery of recombinant gene or silencer gene such as RNA interference (RNAi) into a specific target cell for manipulation of a specific gene expression, and the introduction of DNA vaccine into a specific target cell for targeted antigen presentation in immunology research. An example of application for small molecule delivery can be preclinical studies of electro-chemotherapy into a specific type of cells in cancer research.

Another embodiment of the present invention offers more control over the rate of molecular transport across the membrane due to the narrow distribution of cell-electrode distances. The adhered cells are bound to the capture ligands thus are separated from the electrode surface by an average distance equal to the length of the ligand. Following the application of the voltage to the electrodes, all of the cells experience similar time-dependent electric field and will develop similar distribution of pores on their surfaces. This uniformity of the electric field can be further controlled by applying a pulsed voltage with a timescale sufficiently short to maintain a substantially uniform field local to the cell. In addition, the length of the spacers 55 can be advantageously used as a multiplexing parameter. The electroporation rate of similar cells hybridized at two immobilization regions differing in the spacer length are different. This provides a tool for simultaneously studying the effect of a molecule on the cell behavior as a function of dosage.

In another embodiment, electroporation can be made to be occur at a specific area or location of a cellular species. The cell is first bound to as described in the above embodiments, and the binding is performed using a cellular receptor that is found or concentrated at a specific region on the cellular surface. This provides an orientation of the cell relative to the channel wall. The electric field is then applied at low voltage (below a threshold for electroporation or lysis) for a timescale sufficient to cause ionic screening within the channel liquid, which produces a rapidly decaying and spatially inhomogeneous field profile at the channel wall. The subsequent application of one or more electroporation or electrolysis pulses produces preferential electroporation or cell rupture at the side of the cell closest to the channel wall due to the increased electric field strength in this region.

Antibiotic Susceptibility Testing

Embodiments of the present invention may also be adapted to address a major drawback of current clinical bacteriology methods, namely the need to isolate bacteria on solid agar media when processing a clinical specimen. Even rapidly growing bacteria such as *E. coli* require at least 8 hours to form macroscopic colonies on agar plates. While many aspects of clinical laboratory workflow have been automated by incorporating molecular methods, clinical bacteriology remains highly labor-intensive. Most laboratories currently automate identification and susceptibility testing using either the Vitek (Biomerieux) or Phoenix (Becton-Dickenson) instruments. However, these systems depend on selection of appropriate colonies by expert personnel from overnight growth on agar plates. Several DNA-amplification approaches for clinical bacteriology have been commercialized; however, these efforts have achieved limited market penetration due to high costs, the need for target purification (due to the sensitivity of DNA amplification technology to polymerase inhibitors), the failure to automate the methods, and most importantly the need to lyse the cells which in effect halts their growth and provides only discrete data regarding growth thereby overly complicating estimation of antibiotic susceptibility.

This embodiment of the present invention allows for detection of cell growth in the presence of culture media inoculated with the appropriate antibiotics by detecting the change in fluorescence signal from bacteria over a period of time. This is achieved by injecting the specimen (pre or post culture) through the channel of FIG. 1, whereby the cells are further concentrated using an applied electrical field as already described. The cell concentration at the surface of the reaction zone can be monitored by measuring the fluorescence signal intensity (either due to auto fluorescence, or fluorescence from a labeled receptor bound to the analyte). At this point, the flow of sample is interrupted and the channel is washed. After cell concentration of a desired amount in the reaction zone has been achieved, culture media previously inoculated with the appropriate antibiotics, as determined by the species identification step, is inserted into the channel where it comes into contact with the previously retained cells. An initial fluorescence measurement is obtained to establish a baseline for "no growth". Measurement of subsequent fluorescence signal reveals growth and rate of growth from which susceptibility data can be inferred, as illustrated in FIG. 9.

The change in fluorescence signal can reveal growth which helps to determine the minimum inhibitory concentration (MIC). If auto-fluorescence is used, then the MIC can be determined by measuring the antibiotic dosage at which fluorescence signal growth is reduced beyond a certain level. This can be accomplished by two methods: 1) increasing the antibiotic dosage during growth per one or two multiplication cycles, or 2) have multiple channels that have been previously inoculated with different dosages.

However, it will not allow the determination of minimum bactericidal concentration (MBC) for antibiotics that actually kill the bacterial cells. That can be accomplished by staining the bacteria with an appropriate fluorescent dyes (i.e. vital and mortal stains) such that the signal from dead and live cells can be distinguished. These stains differ in their ability to penetrate healthy bacterial cells. Using these types of stains, and when the fluorescence signal is monitored with appropriate filters, it is possible to determine MIC, MBC, or no growth.

Given that some growth media are highly fluorescent, it may be desirable to use fluorescent stains for common mode rejection. In other words, by using a stain that fluoresces in a certain part of the spectrum in the presence of dead bacteria and a different stain for live bacteria that is spectrally separated, it is possible to null the effects of background fluorescence that is omnipresent in culture media. Additionally, and owing to the fact that certain stains can inhibit bacterial growth, one stain for dead bacteria and scattering signal from the region of growth can be used to accomplish the same common mode rejection.

Lateral Flow Device with Electro Lysis for Rapid Detection

In another embodiment, a test device is provided for determining the presence or absence of cellular analyte in a fluid sample. The test device includes a support and a matrix defining an axial flow path. Typically, the matrix further includes a sample receiving zone and an observation area that contains a capture zone. In a related embodiment, the matrix further includes an absorbent zone disposed downstream of the observation area. Electrodes are provided contacting the capture zone for the electroporation or electro-lysis of cellular analytes bound thereto. Such electroporation or electro-lysis enables the direct detection of cellular analyte by assaying for endogenous moieties such as ATP or enzymes that produce ATP. This embodiment advantageously provides a label-free cellular lateral flow device that overcomes many limitations and problems with prior art devices and methods. In particular, a lateral flow test device and method for the detection of cellular analyte with improved speed and sensitivity are provided.

In a preferred embodiment, the sample receiving zone accepts a fluid sample that may contain cellular analyte. Further, an observation area is disposed downstream of the sample addition zone, and contains an immobilized capture reagent that selectively binds with a cellular antigen. Thus, as the fluid sample flows through the matrix, cellular analyte will bind with the immobile capture reagent in the capture zone of the observation area.

In a particularly preferred embodiment, the cellular analyte of interest is from the group including, but not limited to, *Escherichia coli, Streptococcus* spp., *Enterococcus faecium, Enterococcus faecalis, Staphylococcus aureus*, CoNS, *Strep. Pneumoniae*, Coagulase Negative Staphylococci (*S. epidermidis, S. haemolyticus*), *Enterobacter* (cloacae/aerog.), *Klebsiella* (pneumoniae/oxytoca), *Serratiamarcescens, Proteus mirabilis, Pseudomonas aeruginosa, Acinetobacter baumannii, Stenotrophomonas maltophilia, Candida albicans, Candida tropicalis, Candida parapsilosis, Candida glabrata, Candida krusei*, and *Aspergillus fumigatus*.

In another preferred embodiment, the test device may detect the presence or absence of more than a single cellular antigen. For example, the capture reagent may selectively bind to all members of the *Candida* family. In another example, the capture reagent may selectively bind to all members of the *Enterococcus* family. This may be achieved by a number of means or methods known in the art, such as raising antibodies against broader genus level species, or by mixing multiple antibodies that are each selective to one or more cellular analytes.

In another preferred embodiment, the fluid sample flows along a flow path running from the sample receiving zone (upstream) to the observation area (downstream). Optionally, the fluid may thereafter flow to the absorbent zone.

In a preferred embodiment, the sample receiving zone is made of an absorbent application pad that permits the flow of cells of interest. Suitable materials for manufacturing absorbent application pads include, but are not limited to, hydrophilic polyethylene materials or pads, glass fiber filter paper or pads, desiccated paper, paper pulp, fabric, and the like. In a related embodiment, the sample receiving zone is constructed from any material that absorbs water.

In a preferred embodiment, the absorbent application pad is made of any material from which the fluid sample can pass containing cellular analyte. Further, the absorbent application pad may be constructed to act as a filter for cellular components that are not of interest, hormones, particulate, and other certain substances that may occur in the fluid sample. Application pad materials suitable for use in embodiments of the invention also include those application pad materials disclosed in U.S. Pat. No. 5,075,078, incorporated herein by reference.

In yet another preferred embodiment, the absorbent application pad may incorporate other reagents such as ancillary specific binding members, fluid sample pretreatment reagents, and signal producing reagents.

In another preferred embodiment, the test device is configured to perform an immunological analysis process. In yet another embodiment, the liquid transport along the matrix is based upon capillary action, whereby the liquid transport path can be formed not only by one or more layers of absorbent material, for example paper or fleece, but also by a gap which is sucked full by capillary action.

In a preferred embodiment, the matrix is capable of non-bibulous lateral flow. "Non-bibulous lateral flow" is meant liquid flow in which all of the dissolved or dispersed components of the liquid are carried at substantially equal rates and with relatively unimpaired flow laterally through the membrane, as opposed to preferential retention of one or more components as would occur, e.g., in materials capable of adsorbing or imbibing one or more components.

In a further preferred embodiment, the matrix is made of a typical non-bibulous material such as high density polyethylene sheet material manufactured by Porex Technologies Corp. of Fairburn, Ga., USA. The sheet material has an open pore structure with a typical density, at 40% void volume, of 0.57 gm/cc and an average pore diameter of 1 to 250 micrometers, the average generally being from 3 to 100 micrometers. The optimum pore diameter for the membrane is about 10 to about 50 µm. The membranes typically are from about 1 mil to about 15 mils in thickness, typically in the range of from 5 or 10 mils, but may be up to 200 mils and thicker. In a preferred embodiment, the matrix has a pore size distribution that minimizes non-specific trapping of cellular analyte.

In yet another preferred embodiment, the matrix is made of a material such as untreated paper, cellulose blends, nitrocellulose, polyester, an acrylonitrile copolymer, and the like. The matrix may be constructed to provide either bibulous or non-bibulous flow. In an especially preferred embodiment, the matrix is made of a nonwoven fabric such as Rayon or glass fiber. Other suitable materials include those chromatographic materials disclosed in U.S. Pat. No. 5,075,078, which is herein incorporated by reference. In a preferred embodiment, all or part of the matrix material may be treated with solution that includes blocking and/or stabilizing agents. Blocking agents include bovine serum albumin (BSA), methylated BSA, casein, nonfat dry milk.

In prior art devices requiring a label zone, employment of the selected blocking and stabilizing agents together with colored moieties in the labeling zone followed by the immobilization of the blocking and stabilizing agents on the support (by, e.g., a freeze-drying process, or a forced air heat drying process) is of utmost importance for achieving suitable performance of the device. It is well known that visible moieties, especially particles, aggregate upon air-drying and do not readily rehydrate in contact with a liquid sample. Therefore, absent conversion to the nonbibulous surface, instead of being transported to the capture zone with the sample, the visible moieties will remain trapped in the labeling zone. In contrast, embodiments of the present invention, which do not require such labeling moieties and such blocking and/or stabilizing means, provide a dramatic improvement in the cost, manufacturing yield, long-term stability, and performance.

The observation area may be made of any of the materials listed above, or may be made of a material that is opaque when in a dry state, and transparent when in a moistened state, examples of which include nitrocellulose, nylon, and hydrophilic polyvinylidene difluoride (PVDF). Hydrophilic polyvinylidene difluoride (PVDF) is commercially available form the firm Millipore, Bedford, U.S.A. under trademark Immobilon AV. However, on the basis of the present description, the expert can also select other materials and especially synthetic material membranes which fulfill the above-mentioned conditions. It is believed that the refractive index of the synthetic material is of major influence to this characteristic. It is to be assumed that porous materials, the refractive index of which is close to that of the sample liquid, have the property of becoming transparent in a moist state. In another embodiment, the observation area is made of nylon.

In a preferred embodiment, the capture zone may be constructed from any of the materials as listed above. In a particularly preferred embodiment, the capture zone is made of the same material as the observation zone. Embodiments of the present invention comprise a test device with one or more capture zones.

Further embodiments include capture zones that include microporous materials made from nitrocellulose, by which term is meant any nitric acid ester of cellulose. Thus suitable materials may include nitrocellulose in combination with carboxylic acid esters of cellulose. The pore size of nitrocellulose membranes may vary widely, but is preferably within 5 to 20 microns, preferably 8 to 15 microns. Again, it is optimal to provide a material with a pore size distribution that minimizes non-specific trapping of cellular analyte. To provide non-bibulous flow, these materials may be treated with blocking agents that can block the forces which account for the bibulous nature of bibulous membranes. Suitable blocking agents include bovine serum albumin, methylated bovine serum albumin, whole animal serum, casein, and non-fat dry milk.

In a preferred embodiment, the observation area further includes a procedural control line, to verify that the sample flow is as expected. The control line is a spatially distinct region that includes an immobilized binding member which reacts with a labeled reagent. In a preferred embodiment, the labeled reagent is provided in an additional control label zone that forms a part of the matrix and is located between and in fluid-flow contact with the sample addition zone and the capture zone. Preferably, the control reagent is freeze-dried in the control label zone. More preferably, aforementioned blocking and stabilizing reagents may further be added to the control label zone or sample receiving zone. In another embodiment, the procedural control line contains an authentic sample of the cellular analyte of interest, or a fragment thereof. In another preferred embodiment, the control line contains antibody that is specific for, or otherwise provides for the immobilization of, the labeled reagent. In operation, a labeled reagent binds to the control line, even when the analyte of interest is absent from the test sample.

In a related embodiment, a control conjugate is introduced into the flow sample upstream from the control line. For example, the control conjugate may be added to the fluid sample before the sample is applied to the assay device. Alternatively, the control conjugate may be diffusively bound in the sample receiving zone, or in the control label zone.

In a preferred embodiment, the control conjugate includes a control label and a control reagent. Typically, a control reagent is chosen to be different from the reagent that is recognized by the capture reagent. Further, the control agent is generally not specific for the analyte. In a preferred embodiment, the control reagent binds to a control capture partner that is immobilized on the procedural control line. Thus the control conjugate is directly detected in the control line.

The control label may include streptavidin, and the control capture partner may include biotin, which couples to the avidin specifically. In a particularly preferred embodiment, the control label includes biotin, and the control capture partner includes streptavidin. The artisan will appreciate that other "irrelevant" binding pairs can also be used-such as antigen/antibody reactions unrelated to analyte.

The use of a control line is helpful in that appearance of a signal in the control line indicates the time at which the test result can be read, even for a negative result. Thus, when the expected signal appears in the control line, the presence or absence of a signal in the capture zone can be noted.

In another preferred embodiment, the matrix may further incorporate an absorbent zone. The absorbent zone can act to increase the amount of fluid sample that travels through the capture zone.

In this embodiment, the absorbent zone is located downstream from the capture zone and can be a means for removing excess sample and free label other than the analyte of interest from the matrix of the device. Generally, the absorbent zone will consist of an absorbent material such as filter paper, a glass fiber filter, or the like.

The device may also contain an end of assay control zone indicator. The control zone indicator may consist of a pH indicating reagent (such as bromocresol green) impregnated in the absorbent zone or at a location downstream of the capture zone. Upon contact with the sample, a pH change occurs in the processed matrix. This pH shift converts the pH indicator to a different color (for instance, bromocresol green may be converted from yellow to blue) which is seen in an observation window over the control zone. This technology may also serve as an internal assay control.

The end of assay control zone may be constructed by applying a line of soluble ink on the capture zone (at the interface with the absorbent zone). The liquid front moving through the capture zone will solubilize the ink and transfer it into the absorbent. The resulting color change will be seen in an observation window above the absorbent zone, signifying end of assay.

In a preferred embodiment, the capture reagent binds with the cellular analyte. The capture reagent can be chosen to directly bind the cellular analyte or indirectly bind the analyte by binding with an ancillary specific binding member which is bound to the cellular analyte. In addition, the capture reagent may be immobilized on the solid phase before or during the performance of the assay by means of any suitable attachment method. Typically, the capture site is a delimited or defined portion of the solid phase such that the specific binding reaction of the capture reagent and analyte is localized or concentrated in a limited site, thereby facilitating the detection of signal local to the capture site in contrast to other portions of the solid phase. In a related embodiment, the capture reagent can be applied to the solid phase by dipping, inscribing with a pen, dispensing through a capillary tube, or through the use of reagent jet-printing or other techniques. In addition, the capture zone can be marked, for example with a dye, such that the position of the capture zone upon the solid phase can be visually or instrumentally determined even when there is no label immobilized at the site.

In another embodiment, the observation area includes a negative control area. The purpose of this control area is to alert the user that the test device is not working properly. In a preferred embodiment, the negative control is that part of the observation area outside of the capture zone, and does not include any part of the observation area located directly at or nearby the capture zone. When working properly, no signal or mark should be visible in the negative control area.

The test device preferably includes electrodes for the application of a voltage across the matrix in the capture zone after the sample has been added to the test device and cellular analyte has become bound at the capture zone. The electrodes include a lower electrode provided below the matrix and an upper electrode provided above the matrix. The application of a voltage between the electrodes results in the creation of an internal electric field within the matrix at the capture zone. If the voltage is selected to cause an internal electric field that exceeds the threshold for electroporation of cellular analyte bound at the capture zone, electroporation of the bound cellular analyte will occur. Similarly, if the voltage is selected to cause an internal electric field that exceeds the threshold for electro-lysis of cellular analyte bound at the capture zone, electro-lysis of the bound cellular analyte will occur.

In a preferred embodiment, the test device includes a hollow casing or housing having an application aperture and an observation port. In this embodiment, the flow matrix is contained within the hollow casing, and the fluid sample is added to the matrix through the aperture, which is an opening located in an upstream location on the housing.

Typically, the aperture is located above the sample application pad. In a related embodiment, an aperture may be disposed in any location above the matrix that would provide for facile addition of fluid sample or reagent to the matrix.

Suitable electrode materials include metals such as copper, silver or gold, and other conductive materials. The upper and lower electrodes are electrically connected to contact pads or other suitable contact points on the test device. Exemplary locations for contact pads are on the outer surface of the casing, such as the top surface, side surfaces, or bottom surface. In a preferred embodiment, the contact pads are accessible to mating contact points provided in an automated analyzer or reader.

Preferably, the lower electrode directly contacts the bottom surface of the matrix in the capture zone, so as to be in direct fluidic contact with liquids flowing through the capture zone. The lower electrode preferably comprises a metal foil or a metal sheet. Alternatively, the lower electrode may be deposited onto the top surface of a backing material used to support the matrix in the housing. The lower electrode may extend over the full spatial range of the capture zone, or may extend only in the region where antibodies or other receptors are located.

In a preferred embodiment, the membrane may be backed by a generally water impervious layer, such as mylar, with the lower electrode sandwiched between the layer and membrane. When employed, the backing is generally fastened to the membrane by an adhesive, such as 3M 444 double-sided adhesive tape, with the electrode positioned between the adhesive and the layer. Typically, a water impervious backing is used for membranes of low thickness. A wide variety of polymers may be used provided that they do not bind non-specifically to the assay components and do not interfere with flow of the sample. Illustrative polymers include polyethylene, polypropylene, polystyrene and the like. Alternatively, the membrane may be self supporting. Other non-bibulous membranes, such as polyvinyl chloride, polyvinyl acetate, copolymers of vinyl acetate and vinyl chloride, polyamide, polycarbonate, polystyrene, and the like, can also be used.

The upper electrode is provided in contact with the top side of the capture zone, and is in fluid-flow contact with liquid flowing through the capture zone when the capture zone is moistened. The upper electrode may extend over the full spatial range of the capture zone, or may extend only in the region where antibodies or other receptors are located. The upper electrode may comprise an opaque conductive material or may preferably comprise a transparent electrode that is optionally provided on a transparent substrate. In one embodiment, the transparent electrode is a layer of indium tin oxide coated on a glass substrate.

In another preferred embodiment, the upper and lower electrodes are further used to detect the arrival of the sample fluid front at the capture zone by changes in electrical properties such as conductivity or resistivity of the material between the two electrodes. This provides an additional procedural control for the test device.

The internal field for electroporation or electro-lysis depends on many factors, including the size of and cell wall structure of the cellular analyte, the applied voltage, and the separation between the electrodes. The electric field strength required to achieve a trans-membrane potential of more than 1 V is about 1 kV/cm. Preferably, the applied voltage is selected to provide an internal electric field of at least 1 kV/cm, although this threshold is known to vary for different cell types and species. In an exemplary embodiment, the matrix has a thickness of 5 mil and the applied voltage is at least 12.5 V and is applied for at least 10 microseconds. Depending on the applied field, electroporation can be permanent, or reversible.

The voltage may be applied in as DC or AC voltage, and may be continuous or pulsed. In a preferred embodiment, an AC voltage is applied to limit the formation of bubbles due to electrolysis. Preferably, the voltage is AC, has a frequency between 1 and about 10 MHz. In another preferred embodiment, the voltage is applied in one or more pulses, with each pulse lasting for approximately 10 microseconds to 10 milliseconds. Those skilled in the art will readily appreciate that different combinations of voltage, frequency, pulse duration will be appropriate for different materials, geometries, and cell types.

The detection of a signal due to the presence of one or more cellular antigens bound at the capture zone can be achieved in a number of different embodiments, as disclosed below. Generally, a signal is obtained by providing a signal producing reagent to the capture zone, where it reacts with a signal producing component provided by the electroporated or electro-lysed cellular analyte. In a preferred embodiment, the signal generating reagent is made to flow to the capture zone prior to the application of the voltage.

The signal producing reagent may contain an additional material that allows for the detection and/or confirmation of the presence of the signal producing reagent at the capture zone. Materials that may be included are, but not limited to, chromogenic, luminescent and fluorometric materials. In a preferred embodiment, detection of the presence of the signal producing reagent is provided by a detection system in an automated analyzer or reader.

The signal producing reagent may follow the same flow path as the sample, i.e. it may be applied to the sample port and flow through the label zone to the capture zone. In another embodiment, the signal producing reagent may be added to the capture zone from above, for example, by manual or automated pipettor, dropper or other liquid dispensing means. In another embodiment, the signal producing reagent may be contained within the casing in a sealed compartment or chamber such as a foil pouch, which can be actuated (for example, by opening a valve) or ruptured to cause the signal producing reagent to flow onto the matrix or directly to the capture zone from a lateral direction. In a preferred embodiment, the actuation is provided by an automated analyzer or reader.

In a preferred embodiment, the signal is luminescence. In a preferred embodiment, the signal producing component is adenosine-5'-triphosphate (ATP). In this embodiment, the signal producing reagent is one or more assay known reagents for the assaying of ATP, such as luciferase.

In an alternative embodiment, the signal producing component is an enzyme that generates ATP, for example, adenylate kinase. In this embodiment, the signal producing reagent includes ADP and one or more assay known reagents for the assaying of ATP, such as luciferase In one preferred embodiment in which the signal is luminescence, the casing is adapted to enable a test operator or automated device to remove the upper electrode from the capture zone, thereby enabling the detection of luminescence from the capture zone follow the application of a voltage between the electrodes. In one preferred embodiment, the upper electrode is removably attached to the device. In another preferred embodiment, the upper electrode may be moved axially along the device, and is preferably supporting by the casing. In yet another preferred embodiment, the upper electrode may reside externally as a permanent or disposal external electrode. For example, the upper electrode may be provided and physically applied and/or translated by an automated analyzer or reader.

The present embodiment improves over prior art electroporation devices, particularly those involving closed fluidic cells, by providing an open fluidic environment in which any gas bubbles created by electrolytic processes are readily removed into the surrounding environment.

In another preferred embodiment, the upper electrode may be adapted to apply a compressive force to the capture zone during the application of the voltage. This compressive force may be applied externally by an automated analyzer or reader, or manually. Alternatively, the compressive force may be applied by temporarily or permanently affixing the upper electrode relative to the casing. The compressive force preferably reduces the spacing between the electrodes, which reduces the required voltage for achieving electroporation or electro-lysis. In a preferred embodiment, the compressive force reducing the spacing between electrodes by a factor of two or more.

From the foregoing, it is appreciated that the outer casing or housing of the device may take various forms. Typically, it will include an elongate casing and may have a plurality of interfitting parts. In a particularly preferred embodiment, the housing includes a top cover and a bottom support. In one embodiment, the top cover contains an application aperture and an observation port. In another embodiment, the housing may also contain dividers between the matrix strips to inhibit flow of fluid sample between strips.

In a preferred embodiment, the housing is made of moisture impervious and non-conductive solid material, for example, a plastic material. It is contemplated that a variety of commercially available plastics, including, but not limited to, vinyl, nylon, polyvinyl chloride, polypropylene, polystyrene, polyethylene, polycarbonates, polysulfanes, polyesters, urethanes, and epoxies maybe used to construct a housing. The housing may be prepared by conventional methodologies, such as standard molding technologies that are well known and used in the art. The housing may be produced by molding technologies which include, but are not limited to, injection molding, compression molding, transfer molding, blow molding, extrusion molding, foam molding, and thermoform molding. The aforementioned molding technologies are well known in the art and so are not discussed in detail herein. See for example, Processes And Materials Of Manufacture, Third Edition, R. A. Lindsberg (1983) Allyn and Baron pp. 393-431.

It will be appreciated by one skilled in the art that a test strip device can be made of more than one material (e.g., different zones or sites can be made of different materials) and a flow-through device can have more than one layer, wherein different layers can be made of different materials, so long as the multiple materials or layers are in fluid-flow contact with one another thereby enabling the passage of test sample between the materials or layers. Fluid-flow contact permits the passage of at least some components of the test sample between the zones or layers of the device. Fluid-flow is preferably uniform along the contact interface between the different zones or layers. Different reagents may be disposed on different materials, and different reagents may be disposed on different zones.

Embodiments of the present invention are particularly suitable for a test device as shown in the accompanying drawings, and described in detail as follows. It is understood that the drawings are provided for purposes of illustration and not meant limit the scope of the present invention.

Figure 13:
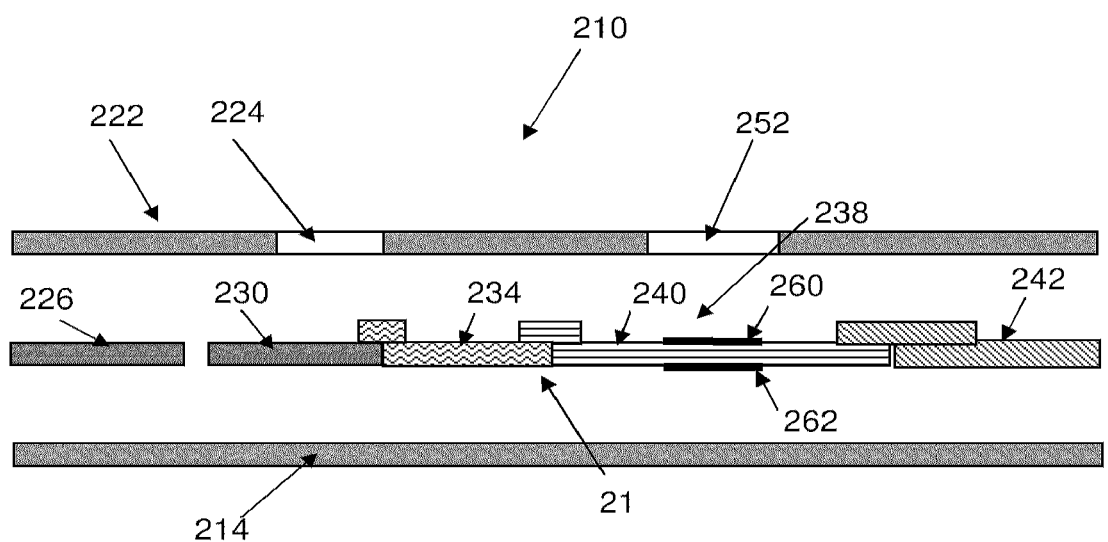
FIG. 13 shows a lateral flow device comprising electrodes for detecting cellular analyte.

FIG. 13 shows a first embodiment of a test device 10 constructed in accordance with a preferred embodiment of the present invention. The example is provided for the purpose of teaching a preferred embodiment and is not intended to limit the scope of the invention in any way.

Test device 210 has a bottom support 214, a flow matrix 218, a top cover 222, and an optional desiccant 226. In its longitudinal direction, matrix 218 can be subdivided into a sample application zone 230, an optional control label zone 234, an observation area 238, and an absorbent zone 242. The Figure shows the device schematically in an expanded view where the top cover 222 and bottom support 214 are vertically displaced for illustration purposes.

The sample application zone is located at an upstream location on matrix 218, and is configured to receive the fluid sample. Control label zone 234 is optionally located downstream of application zone 230 and contains label reagent for use with an optional control line. The observation area is located downstream of the label zone, and includes a capture zone 240 that contains capture reagent. Absorbent pad 242 is located downstream of observation area 38.

Top cover 222 has an application aperture 248 disposed above the sample application pad, and an observation port 252 disposed above the observation area. In cooperation, the top cover and the bottom support are configured to provide a housing for matrix 218 and desiccant 226. As shown, the desiccant is typically positioned separately from the matrix. Upper 260 and lower 262 electrodes are provided above and below the capture zone, respectively. Capture zone 240 optionally includes an immobilized control line that selectively binds the label reagent provided in the optional label zone.

In operation, the sample fluid is added through aperture 248, and on to application pad 230. The fluid sample is transported from application pad 230 to the optional label zone 234, where the fluid elutes labeled reagent. If the label zone is not provided, the fluid sample flows from the sample application pad to the capture zone.

Next, the fluid sample is advanced to observation area 238, and then on to the absorbent zone. Observation area 238, now moistened by the sample fluid, may become transparent. Cellular analyte binds to receptors immobilized in the capture zone 240 within the observation zone 238. The fluid front progresses axially along the matrix and is absorbed by the absorbent pad 242.

In a preferred embodiment, prior to the application of a voltage to the upper 260 and lower 262 electrodes, a signal producing reagent is first transported to the capture zone. As described above, this may be achieved by many different methods that will be apparent to those skilled in the art. Exemplary methods including adding the signal producing reagent to the sample application pad 230, which will flow axially along the matrix to the capture zone, or directly adding the signal producing reagent to the capture zone from above the capture zone 240 (through the observation port 252).

The application of a voltage to the upper 260 and lower 262 electrodes causes cellular analyte bound in the capture zone 240 to be electroporated or electro-lysed (depending on the nature of the applied voltage). If signal producing reagent has not been added prior to the application of the voltage, the signal producing reagent is subsequently added by means including those described in the preceding paragraph. Preferably, the upper electrode applies a compression force to the capture zone while the voltage is applied, which reduces the spacing between the electrodes and lowers the threshold voltage that is required for electroporation or electro-lysis. More preferably, the compressive force is applied by an automated analyzer or reader.

Following the application of the voltage, cellular analyte bound at the capture zone 240 makes available signal producing component, which can react with the signal producing reagent to produce a signal. The signal producing component may be made available by electro-lysis, in which the signal producing component is released into the fluid in the capture zone 240, or it may be make available following electroporation by allowing signal producing reagent to enter the cellular analyte and react with the signal producing component internally, or both internally and externally, to the cellular analyte cell wall.

As described above, the signal is preferably an optical signal and is more preferably luminescence, but it may also be chromogenic or fluorometric. The signal producing reagent is preferably luciferase and the signal producing component is preferably ATP. Optical emission comprising the signal may be detected by an imager such as a CCD or CMOS imager. Preferably, the imager is housed within an automated analyzer or reader. The analyzer or reader may include translation means such as linear motors to scan an area of the capture zone.

To enable the imaging of a test device in which the signal is optical emission, the upper electrode 260 may be removed prior to imaging. The electrode may be removed manually or may be removed by an automated analyzer. Preferably, the upper electrode is translated axially along the device to render the capture zone accessible to the imager. Alternatively, the upper electrode may form an external component of a test device kit, and may be applied and removed by an automated analyzer or reader. More preferably, the upper electrode 260 is a transparent conductor, such as indium tin oxide, which may be provided on a transparent substrate. In such an embodiment, the optical power comprising the signal may be directly imaged or detected without needed to move or remove the upper electrode 260.

After imaging or detecting the optical emission from the test device, the signal is related to a bacterial contcentration, or a positive/negative result, by virtue of pre-established calibration data or a pre-established calibration curve. Such calibration information can be obtained by assaying samples containing known concentrations of cellular analyte, as is known in the art.

Embodiments of the invention are not intended to be limited to a single test device, and embodiments further contemplate a multi-cellular-analyte device. For example, the test device may include more than one capture zone, wherein capture zones are located serially and axially along the matrix, and each capture zone has therein a unique receptor targeted at a unique cellular analyte. In another preferred embodiment, the test device may comprise multiple parallel flow devices in fluid-flow connection with one or more sample pads, with the set of devices contained in a single housing. In a more preferred embodiment, a multi-strip device comprising multiple parallel test devices is provided, with multiple capture zones per parallel test device, where each capture zone is in fluid contact with upper and lower electrodes when moistened.

In a further embodiment of the invention, cellular analyte that is electroporated or electro-lysed makes genetic molecules such as DNA or RNA available in the capture zone, where it may bind to additional molecular receptors located within the capture zone or downstream from the capture zone, in a supplemental molecular capture zone that is within the observation zone. Additional molecular labeled reagents, for example, labeled DNA or PNA oligonucleotides, may be provided to the capture zone to enable detection. For example, molecular labeled reagents may be provided in the sample addition zone, in the optional label zone, or added directly to the capture zone via external liquid dispensing means such as a pipettor.

The following examples are presented to enable those skilled in the art to understand and to practice the present invention. They should not be considered as a limitation on the scope of the invention, but merely as being illustrative and representative thereof.

EXAMPLES

Example 1

Preparation of Immobilization Regions Comprising Antibodies or Nucleic Acid Probes In one example, a solid support is prepared for the immobilization of either an antibody recognizing a cell surface or a nucleic acid probe for binding intracellular nucleic acids. Polished aluminum bottom plates were cleaned with water then rinsed twice with methanol and air-dried. 2% 3-Aminopropyl Triethoxysilane was prepared in 95% Methanol 5% water and the plates were immersed in silane for 5 min. Then, the plates were rinsed in methanol twice, air-dried and baked at 110° C. for 10 min. After cooling, the plates were immersed in 2.5% glutaraldehyde homobifunctional crosslinker in phosphate buffered saline, pH 7.4 for 1 hour, thoroughly rinsed in water and air-dried. The reaction zone of the microfluidic channel was defined by applying a double-sided adhesive spacer on the treated surface of the aluminum plates. Amino-labeled capture oligonucleotide probe of 1 uM final concentration which recognizes 16S rRNA of $E.\ coli$ or goat anti-$E.\ coli$ antibody (Abcam) of 50 ug/mL final concentration in 10 mM carbonate buffer pH 9 was spotted on the reaction zone of prepared aluminum plates and incubated in a humidified chamber at room temperature for 1 hr or at 4° C. overnight. Unbound antibody or probe was washed from the surface with water and the reaction zone was blocked with 02% bovine serum albumin and 0.1% Tween-20 in PBS pH 7.4 at room temperature for 1 hr. After washing with water, the plates were air-dried and the microfluidic channels were assembled by applying the top plate on the adhesive spacer.

Example 2

Figure 14:
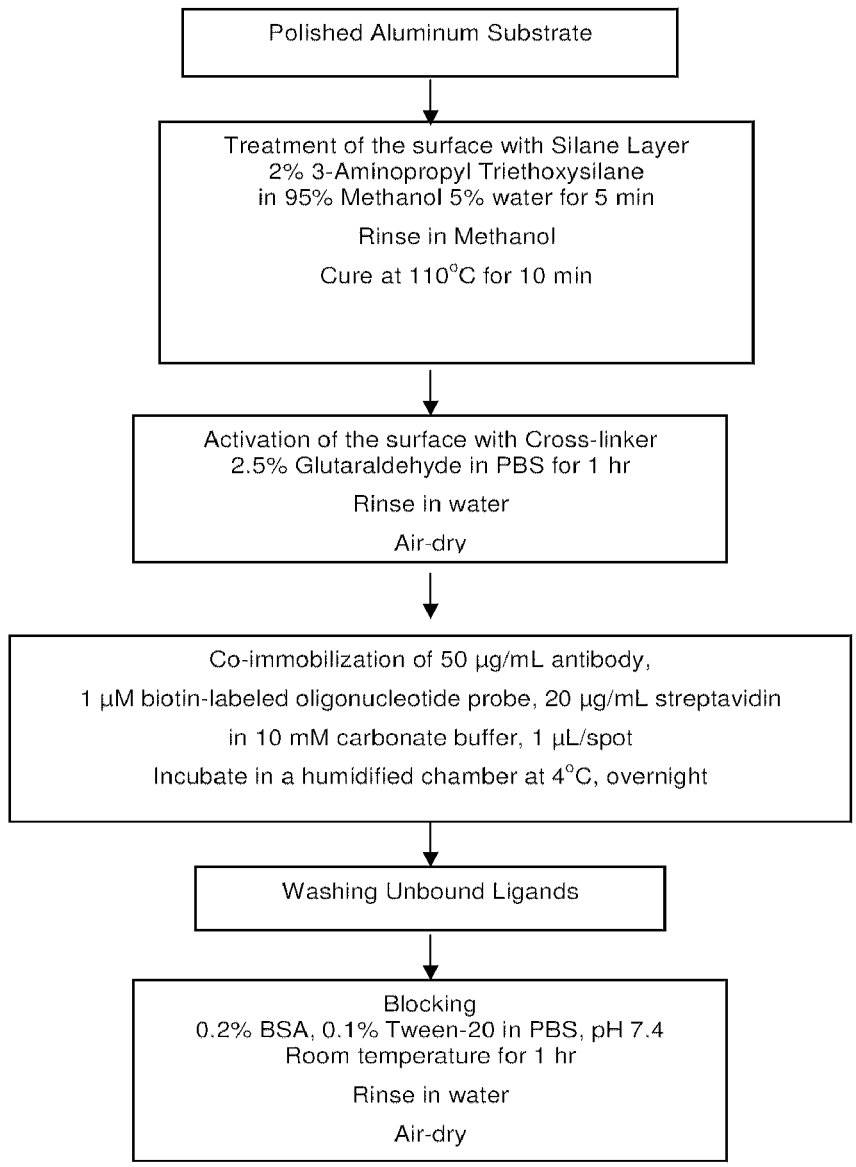
FIG. 14 illustrates the steps taken to prepare an array of co-immobilized antibody and capture oligonucleotide probes.

Preparation of Immobilization Regions Comprising Antibodies and Nucleic Acid Probes In a second example, the above protocol was adapted to support the co-immobilization of antibody and nucleic acid probes within a common immobilization region. The method is schematically illustrated in the flow chart shown in FIG. 14, as henceforth described. 1 μM final concentration of biotin-labeled capture oligonucleotide probe was mixed with 20 μg/mL of Streptavidin (Sigma) in 10 mM carbonate buffer pH 9 for 5 min, and then goat anti-$E.\ coli$ antibody (Abcam) of 50 ug/mL final concentration was added. The antibody and probe mixture was spotted on the reaction zone of prepared aluminum plates, therefore forming a common immobilization region, and incubated in a humidified chamber at 4° C. overnight. Unbound materials were washed from the surface with water and the reaction zone was blocked with 0.2% bovine serum albumin and 0.1% Tween-20 in PBS pH 7.4 at room temperature for 1 hr. After washing with water, the plates were air-dried and the microfluidic channels were assembled by applying the top plate on the adhesive spacer.

In order to demonstrate the effectiveness of the foretold receptor immobilization method, two reaction channels were constructed. Each channel has three zones; the first zone, indicated by "Anti-Bacteria Antibodies" in FIG. 15, has two identical immobilization regions with antibodies immobilized following the method of Example 1. The second zone, indicated by "rRNA capture probes" in FIG. 15, has two identical immobilization regions with nucleic acid probes immobilized following the method of Example 1. The third zone, indicated by "Hybrid biosite" in FIG. 15, has two identical immobilization regions with antibody and nucleic acid probes co-immobilized following the method of Example 2.

$Escherichia\ coli$ DH5-α strain was re-suspended in PBS as $10^8$ CFU/mL. The bacteria suspension in 50 μL volume was flowed into the channel #1, indicated by "Whole bacteria sample" in FIG. 15. After 10 minutes of incubation at room temperature, the channel was washed through with 100 μL volume of water for 5 times. Then, the channel was filled with 2 μg/mL of peroxidase-conjugated goat anti-$E.\ coli$ antibody in the blocking buffer. After incubation for 10 min at room temperature, the channel was washed with water for 5 times and filled with TMB peroxidase substrate for membrane (sigma) to detect the captured bacteria. The result is shown in FIG. 15.

Figure 15:
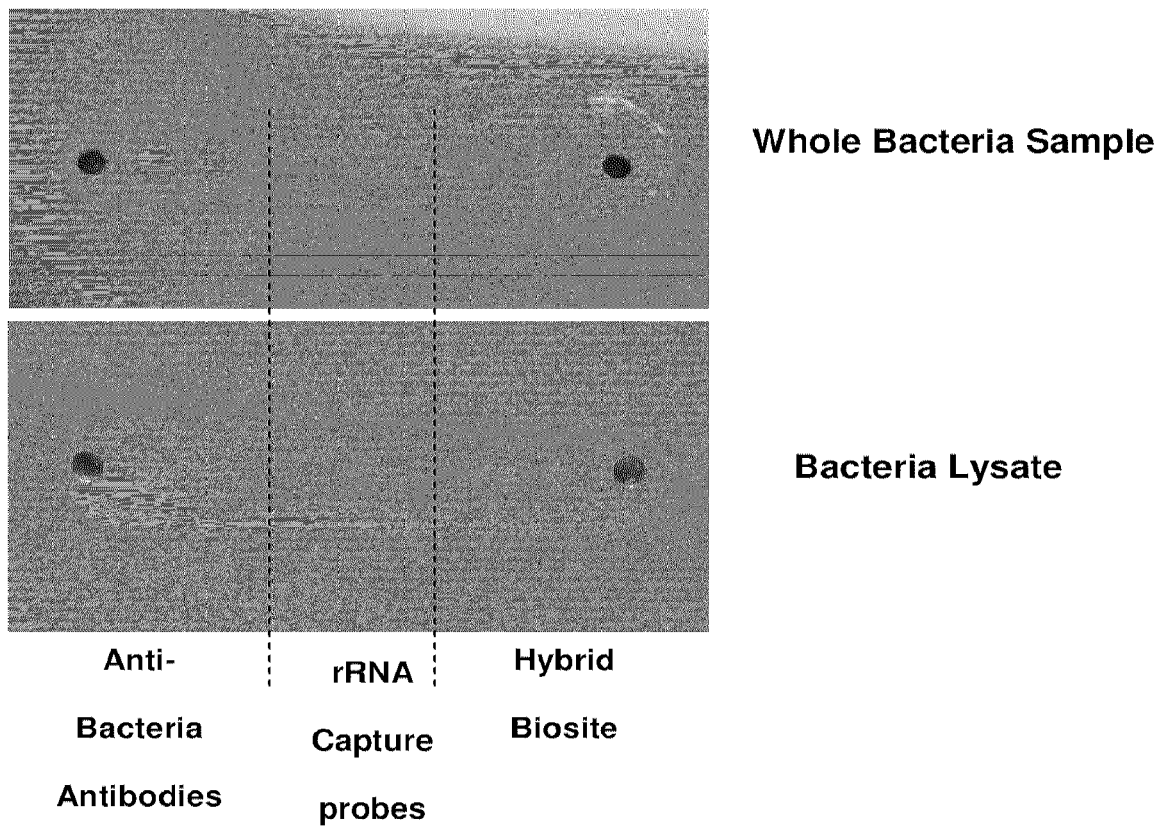
FIG. 15 illustrates a comparison of analyte capture by single and co-immobilized capture probes.

The second channel, indicated by "Bacteria lysate" in FIG. 15, was used to detect 16S rRNA. $Escherichia\ coli$ DH5-α strain was re-suspended in deionized water as $10^8$ CFU/mL and bacterial cell lysis was allowed for 10 min. The lysed bacteria in 20 μL volume was mixed with 20 μL volume of 0.5 μM FITC-labeled detector probe in 500 mM phosphate buffer pH 7.4. The mixture was flowed into the channel and incubated for 10 min at 46° C. The channel was washed with water for 5 times and filled with peroxidase-conjugated anti-FITC antibody (Chemicon), diluted 1:1000 in the blocking buffer. After incubation for 10 min at room temperature, the channel was washed with water for 5 times and filled with TMB to detect the bound bacterial rRNA. The result is shown in FIG. 15. It can be easily noted that the performance of the hybrid immobilization region is similar to the biosite having individual receptors.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

Therefore what is claimed is:
1. A microfluidic device for disrupting a cellular membrane of a cell, said device comprising:
   a microfluidic channel for flowing a cell-containing liquid sample;
   a first electrode provided on one surface of said microfluidic channel, said first electrode comprising aluminum etched with a dense network of microscopic tunnels;

a second electrode provided on an opposing surface of said microfluidic channel;
an aluminum oxide dielectric layer formed on said first electrode by electrochemical oxidation, for preventing the flow of a Faradaic current within said microfluidic channel under the application of a voltage between said first electrode and said second electrode; and
a voltage source connected to said first electrode and said second electrode for applying a pulsed voltage therebetween.

2. The device according to claim 1 wherein said aluminum oxide dielectric layer comprises an immobilization region, said immobilization region having provided thereon an adherent material for immobilizing one or more cells of said cell-containing liquid sample.

3. The device according to claim 2 wherein said first electrode and said second electrode extend upstream of said immobilization region, such that said cells may be concentrated to upstream of immobilization region under the application of a series of unipolar voltage pulses between said first electrode and said second electrode.

4. A method of disrupting a cellular membrane of one or more cells provided in a cell-containing liquid sample, said method comprising the steps of:
providing a microfluidic device comprising:
a microfluidic channel;
a first electrode provided on one surface of said microfluidic channel, wherein first electrode comprises aluminum etched with a dense network of microscopic tunnels;
a second electrode provided on an opposing surface of said microfluidic channel;
an aluminum oxide dielectric layer formed on said first electrode by electrochemical oxidation, for preventing the flow of a Faradaic current within said microfluidic channel under the application of a voltage between said first electrode and said second electrode; and
a voltage source connected to said first electrode and said second electrode for applying a pulsed voltage therebetween;
flowing said cell-containing liquid sample through said microfluidic channel; and
applying one or more voltage pulses to said electrodes, said voltage pulses having an effective time duration and an amplitude for disruption of a cellular membrane of said cells.

5. The method according to claim 4 wherein each pulse of said voltage pulses has a time duration on a millisecond to sub-millisecond timescale.

6. The method according to claim 4 wherein said disruption of said cellular membrane includes electro-lysis of said cellular membrane.

7. The method according to claim 4 wherein said aluminum oxide dielectric layer comprises an immobilization region, said immobilization region having provided thereon an adherent material for immobilizing one or more cells, such that the one or more cells are immobilized by said immobilization region prior to application of the voltage pulses.

8. The method according to claim 7 wherein said immobilization region further comprises secondary receptors for binding intracellular analyte released from said immobilized cells, said method further comprising the step of detecting intracellular analyte bound to said secondary receptors.

9. The method according to claim 8 wherein said step of detecting intracellular analyte include:
flowing a detector reagent into said microfluidic channel, said detector reagent comprising a labeled receptor specific to said intracellular analyte; and
flowing a wash reagent through said microfluidic channel; and
detecting a signal from detector reagent bound to intracellular analyte bound to said secondary receptors.

10. The method according to claim 8 wherein said intracellular analyte includes rRNA and wherein said secondary receptors include are DNA probes or synthetic DNA analog probes.

11. The method according to claim 7 wherein said device further comprises one or more additional immobilization regions, wherein said immobilization region and said additional immobilization regions form an array.

12. The method according to claim 11 wherein each said immobilization region is selective to a different intracellular analyte.

13. The method according to claim 12 wherein said adherent material within each said immobilization region is selective to cell genus, cell species, or cell strain.

14. The microfluidic device according to claim 1 wherein a thickness of said aluminum oxide dielectric layer is in the range of approximately 10 nm to 100 nm.

15. The microfluidic device according to claim 1 wherein said second electrode is a transparent electrode.

16. The microfluidic device according to claim 2 wherein said adherent material comprises primary receptors having an affinity for a surface of said cells.

17. The microfluidic device according to claim 16 wherein said primary receptors are antibodies.

18. The microfluidic device according to claim 2 wherein said adherent material is capable of immobilizing more than one cell type or genus.

19. The microfluidic device according to claim 2 wherein said immobilization region further comprising secondary receptors for binding intracellular analyte released from said cells.

20. The microfluidic device according to claim 19 wherein said secondary receptors are immobilized to said adherent material.

21. The microfluidic device according to claim 19 wherein said secondary receptors are selected from the group consisting of antibodies, aptamers, nucleic acids, and nucleic acid analogs.

22. The microfluidic device according to claim 19 wherein said cells are prokaryotic cells and wherein said intracellular analyte comprises a nucleic acid.

23. The microfluidic device according to claim 19 wherein said intracellular analyte is specific to one of a type of said cell and a genus comprising said cell.

24. The microfluidic device according to claim 2 further comprising one or more additional immobilization regions, wherein said immobilization region and said additional immobilization regions form an array.

25. The microfluidic device according to claim 24 wherein each said immobilization region is selective to a different intracellular analyte.

26. The microfluidic device according to claim 25 wherein said adherent material within each said immobilization region is selective to a unique cell type or genus.

27. The microfluidic device according to claim 26 wherein each said immobilization region is provided for detecting a unique type, species, strain, and/or genus of a microorganism.

* * * * *